(12) United States Patent
Hawkins et al.

(10) Patent No.: US 12,089,873 B2
(45) Date of Patent: *Sep. 17, 2024

(54) SKIN FOUNDATION ACCESS PORTAL

(71) Applicant: Medos International Sarl, Le Locle (CH)

(72) Inventors: J. Riley Hawkins, Cumberland, RI (US); Christopher Ramsay, West Wareham, MA (US); Thomas Gamache, Westport, MA (US); Eric Buehlmann, Duxbury, MA (US)

(73) Assignee: Medos International Sàrl, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/567,088

(22) Filed: Dec. 31, 2021

(65) Prior Publication Data

US 2022/0117626 A1    Apr. 21, 2022

Related U.S. Application Data

(63) Continuation of application No. 16/362,488, filed on Mar. 22, 2019, now Pat. No. 11,241,252.

(51) Int. Cl.
*A61B 17/34* (2006.01)
*A61B 17/02* (2006.01)

(52) U.S. Cl.
CPC ...... *A61B 17/3423* (2013.01); *A61B 17/0218* (2013.01); *A61B 17/3462* (2013.01); *A61B 17/3415* (2013.01); *A61B 2017/348* (2013.01)

(58) Field of Classification Search
CPC ............ A61B 17/3415; A61B 17/3417; A61B 17/3421; A61B 17/3423;

(Continued)

(56) References Cited

U.S. PATENT DOCUMENTS 4,573,448 A    3/1986   Kambin
4,646,738 A    3/1987   Trott
(Continued)

FOREIGN PATENT DOCUMENTS

CN     106999210 B     10/2020
JP     H10290797 A     11/1998
(Continued)

OTHER PUBLICATIONS

International Search Report and Written Opinion for Application No. PCT/US2015/043554, dated Nov. 19, 2015 (8 pages).

(Continued)

*Primary Examiner* — Anu Ramana
(74) *Attorney, Agent, or Firm* — Barnes & Thornburg LLP

(57) ABSTRACT

Surgical access stabilization devices, systems, and methods are disclosed herein. For example, the devices, systems, and methods disclosed herein can be used during a surgical procedure to selectively establish, stabilize, and maintain a desired trajectory and/or positioning of a surgical access device. An exemplary surgical access stabilization device can include a pad with an adhesive distal facing surface to adhere to an anchor surface, a surgical access device coupled to the pad, and a locking mechanism to selectively lock a position of the surgical access device relative to the pad. In one embodiment, the anchor surface can be the skin of a patient. An exemplary surgical access device stabilization method can include making an incision in a patient at a surgical site, inserting a surgical access device through the incision, adhering a pad to an anchor surface, e.g., the skin of the patient, coupling the surgical access device to the pad, and selectively locking a position of the surgical access device relative to the pad. Other exemplary devices, systems, and methods are also provided.

16 Claims, 24 Drawing Sheets

(58) Field of Classification Search
CPC .... A61B 2017/3407; A61B 2017/3445; A61B 2017/348; A61B 90/50
See application file for complete search history.

(56) References Cited

U.S. PATENT DOCUMENTS

| | | | |
|---|---|---|---|
| 4,678,459 A | 7/1987 | Onik et al. | |
| 4,795,435 A | 1/1989 | Steer | |
| 4,863,430 A | 9/1989 | Klyce et al. | |
| 4,888,146 A | 12/1989 | Dandeneau | |
| 5,080,662 A | 1/1992 | Paul | |
| 5,137,520 A * | 8/1992 | Maxson | A61M 25/02 128/DIG. 26 |
| 5,195,541 A | 3/1993 | Obenchain | |
| 5,263,939 A * | 11/1993 | Wortrich | A61B 17/34 604/174 |
| 5,285,795 A | 2/1994 | Ryan et al. | |
| 5,395,317 A | 3/1995 | Kambin | |
| 5,439,464 A | 8/1995 | Shapiro | |
| 5,529,580 A | 6/1996 | Kusunoki et al. | |
| 5,540,706 A | 7/1996 | Aust et al. | |
| 5,569,290 A | 10/1996 | McAfee | |
| 5,591,187 A | 1/1997 | Dekel | |
| 5,601,569 A | 2/1997 | Pisharodi | |
| 5,662,300 A | 9/1997 | Michelson | |
| 5,688,222 A | 11/1997 | Hluchy et al. | |
| 5,730,754 A | 3/1998 | Obenchain | |
| 5,733,242 A | 3/1998 | Rayburn et al. | |
| 5,735,792 A | 4/1998 | Vanden Hoek et al. | |
| 5,820,623 A | 10/1998 | Ng | |
| 5,885,300 A | 3/1999 | Tokuhashi et al. | |
| 5,894,369 A | 4/1999 | Akiba et al. | |
| 5,899,425 A | 5/1999 | Corey Jr. et al. | |
| 5,954,635 A | 9/1999 | Foley et al. | |
| 6,033,105 A | 3/2000 | Barker et al. | |
| 6,053,907 A | 4/2000 | Zirps | |
| 6,063,021 A | 5/2000 | Hossain et al. | |
| 6,110,182 A | 8/2000 | Mowlai-Ashtiani | |
| 6,200,322 B1 | 3/2001 | Branch et al. | |
| 6,217,509 B1 | 4/2001 | Foley et al. | |
| 6,234,961 B1 | 5/2001 | Gray | |
| 6,283,966 B1 | 9/2001 | Houfburg | |
| 6,286,179 B1 | 9/2001 | Byrne | |
| 6,296,644 B1 | 10/2001 | Saurat et al. | |
| 6,322,498 B1 | 11/2001 | Gravenstein et al. | |
| 6,354,992 B1 | 3/2002 | Kato | |
| 6,371,968 B1 | 4/2002 | Kogasaka et al. | |
| 6,383,191 B1 | 5/2002 | Zdeblick et al. | |
| 6,447,446 B1 | 9/2002 | Smith et al. | |
| 6,468,289 B1 | 10/2002 | Bonutti | |
| 6,558,407 B1 | 5/2003 | Ivanko et al. | |
| 6,575,899 B1 | 6/2003 | Foley et al. | |
| 6,579,281 B2 | 6/2003 | Palmer et al. | |
| 6,626,830 B1 | 9/2003 | Califiore et al. | |
| 6,648,915 B2 | 11/2003 | Sazy | |
| 6,676,597 B2 | 1/2004 | Guenst et al. | |
| 6,688,564 B2 | 2/2004 | Salvermoser et al. | |
| 6,758,809 B2 | 7/2004 | Briscoe et al. | |
| 6,808,505 B2 | 10/2004 | Kadan | |
| 6,887,198 B2 | 5/2005 | Phillips et al. | |
| 6,983,930 B1 | 1/2006 | La Mendola et al. | |
| 7,087,058 B2 | 8/2006 | Cragg | |
| 7,104,986 B2 | 9/2006 | Hovda et al. | |
| 7,137,949 B2 | 11/2006 | Scirica et al. | |
| 7,182,731 B2 | 2/2007 | Nguyen et al. | |
| 7,341,556 B2 | 3/2008 | Shalman | |
| 7,434,325 B2 | 10/2008 | Foley et al. | |
| 7,591,790 B2 | 9/2009 | Pflueger | |
| 7,594,888 B2 | 9/2009 | Raymond et al. | |
| 7,618,431 B2 | 11/2009 | Roehm, III et al. | |
| 7,636,596 B2 | 12/2009 | Solar | |
| 7,637,905 B2 | 12/2009 | Saadat et al. | |
| 7,641,659 B2 | 1/2010 | Emstad et al. | |
| 7,771,384 B2 | 8/2010 | Ravo | |
| 7,794,456 B2 | 9/2010 | Sharps et al. | |
| 7,811,303 B2 | 10/2010 | Fallin et al. | |
| 7,905,833 B2 * | 3/2011 | Brister | A61B 5/1486 600/347 |
| 7,931,579 B2 | 4/2011 | Bertolero et al. | |
| 7,946,981 B1 | 5/2011 | Cubb | |
| 7,951,141 B2 | 5/2011 | Sharps et al. | |
| 7,959,564 B2 | 6/2011 | Ritland | |
| 7,988,623 B2 | 8/2011 | Pagliuca et al. | |
| 8,007,492 B2 | 8/2011 | DiPoto et al. | |
| 8,038,606 B2 | 10/2011 | Otawara | |
| 8,043,381 B2 | 10/2011 | Hestad et al. | |
| 8,062,218 B2 | 11/2011 | Sebastian et al. | |
| 8,092,464 B2 | 1/2012 | McKay | |
| 8,096,944 B2 | 1/2012 | Harrel | |
| 8,202,216 B2 | 6/2012 | Melkent et al. | |
| 8,236,006 B2 | 8/2012 | Hamada | |
| 8,333,690 B2 | 12/2012 | Ikeda | |
| 8,360,970 B2 | 1/2013 | Mangiardi | |
| 8,372,131 B2 | 2/2013 | Hestad et al. | |
| 8,382,048 B2 | 2/2013 | Nesper et al. | |
| 8,397,335 B2 | 3/2013 | Gordin et al. | |
| 8,435,174 B2 | 5/2013 | Cropper et al. | |
| 8,460,180 B1 | 6/2013 | Zarate et al. | |
| 8,460,186 B2 | 6/2013 | Ortiz et al. | |
| 8,460,310 B2 | 6/2013 | Stern | |
| 8,518,087 B2 | 8/2013 | Lopez et al. | |
| 8,535,220 B2 | 9/2013 | Mondschein | |
| 8,556,809 B2 | 10/2013 | Vijayanagar | |
| 8,585,726 B2 | 11/2013 | Yoon et al. | |
| 8,602,979 B2 | 12/2013 | Kitano | |
| 8,622,894 B2 | 1/2014 | Banik et al. | |
| 8,636,655 B1 | 1/2014 | Childs | |
| 8,690,764 B2 | 4/2014 | Clark et al. | |
| 8,721,536 B2 | 5/2014 | Marino et al. | |
| 8,740,779 B2 | 6/2014 | Yoshida | |
| 8,784,421 B2 | 7/2014 | Carrison et al. | |
| 8,821,378 B2 | 9/2014 | Morgenstern Lopez et al. | |
| 8,834,507 B2 | 9/2014 | Mire et al. | |
| 8,845,734 B2 | 9/2014 | Weiman | |
| 8,852,242 B2 | 10/2014 | Morgenstern Lopez et al. | |
| 8,870,753 B2 | 10/2014 | Boulais et al. | |
| 8,870,756 B2 | 10/2014 | Maurice | |
| 8,876,712 B2 | 11/2014 | Yee et al. | |
| 8,894,573 B2 | 11/2014 | Loftus et al. | |
| 8,894,653 B2 | 11/2014 | Solsberg et al. | |
| 8,926,502 B2 | 1/2015 | Levy et al. | |
| 8,926,592 B2 * | 1/2015 | Blott | A61M 3/0229 604/9 |
| 8,932,207 B2 | 1/2015 | Greenburg et al. | |
| 8,932,360 B2 | 1/2015 | Womble et al. | |
| 8,936,605 B2 | 1/2015 | Greenberg | |
| 8,974,381 B1 | 3/2015 | Lovell et al. | |
| 8,986,199 B2 | 3/2015 | Weisenburgh, II et al. | |
| 8,992,580 B2 | 3/2015 | Bar et al. | |
| 9,028,522 B1 | 5/2015 | Prado | |
| 9,050,146 B2 | 6/2015 | Woolley et al. | |
| 9,055,936 B2 | 6/2015 | Mire et al. | |
| 9,072,431 B2 | 7/2015 | Adams et al. | |
| 9,078,562 B2 | 7/2015 | Poll et al. | |
| 9,131,948 B2 | 9/2015 | Fang et al. | |
| 9,144,374 B2 | 9/2015 | Maurice, Jr. | |
| 9,198,674 B2 | 12/2015 | Benson et al. | |
| 9,211,059 B2 | 12/2015 | Drach et al. | |
| 9,216,016 B2 | 12/2015 | Fiechter et al. | |
| 9,216,125 B2 | 12/2015 | Sklar | |
| 9,232,935 B2 | 1/2016 | Brand et al. | |
| 9,247,997 B2 | 2/2016 | Stefanchik et al. | |
| 9,265,491 B2 | 2/2016 | Lins et al. | |
| 9,277,928 B2 | 3/2016 | Morgenstern Lopez | |
| 9,307,972 B2 | 4/2016 | Lovell et al. | |
| 9,320,419 B2 | 4/2016 | Kirma et al. | |
| RE46,007 E | 5/2016 | Banik et al. | |
| RE46,062 E | 7/2016 | James et al. | |
| 9,386,971 B1 | 7/2016 | Casey et al. | |
| 9,387,313 B2 | 7/2016 | Culbert et al. | |
| 9,414,828 B2 | 8/2016 | Abidin et al. | |
| 9,486,296 B2 | 11/2016 | Mire et al. | |
| 9,492,194 B2 | 11/2016 | Morgenstern Lopez et al. | |
| 9,510,853 B2 | 12/2016 | Aljuri et al. | |

(56) References Cited

U.S. PATENT DOCUMENTS

| | | | |
|---|---|---|---|
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,694,130 B2 * | 7/2017 | Andino .............. A61M 25/02 |
| 9,700,378 B2 | 7/2017 | Mowlai-Ashtiani |
| 9,706,905 B2 | 7/2017 | Levy |
| 11,000,213 B2 * | 5/2021 | Kamath .............. A61B 5/1451 |
| 11,241,252 B2 | 2/2022 | Hawkins et al. |
| 2002/0022762 A1 | 2/2002 | Beane et al. |
| 2002/0138020 A1 | 9/2002 | Pflueger |
| 2003/0083555 A1 | 5/2003 | Hunt et al. |
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |
| 2005/0085692 A1 | 4/2005 | Kiehn et al. |
| 2005/0090848 A1 | 4/2005 | Adams |
| 2005/0187570 A1 | 8/2005 | Nguyen et al. |
| 2005/0256525 A1 | 11/2005 | Culbert et al. |
| 2006/0089625 A1 | 4/2006 | Voegele et al. |
| 2006/0206118 A1 | 9/2006 | Kim et al. |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0203396 A1 | 8/2007 | McCutcheon et al. |
| 2007/0225556 A1 | 9/2007 | Ortiz et al. |
| 2007/0260113 A1 | 11/2007 | Otawara |
| 2008/0015621 A1 | 1/2008 | Emanuel |
| 2008/0033251 A1 | 2/2008 | Araghi |
| 2008/0081951 A1 | 4/2008 | Frasier et al. |
| 2008/0188714 A1 | 8/2008 | McCaffrey |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2011/0028791 A1 | 2/2011 | Marino et al. |
| 2011/0028797 A1 | 2/2011 | Yee et al. |
| 2011/0054507 A1 | 3/2011 | Batten et al. |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0295070 A1 | 12/2011 | Yasunaga |
| 2011/0319941 A1 | 12/2011 | Bar et al. |
| 2012/0022368 A1 | 1/2012 | Brabrand et al. |
| 2012/0095296 A1 | 4/2012 | Trieu et al. |
| 2012/0101338 A1 | 4/2012 | Cormac |
| 2012/0184956 A1 | 7/2012 | Velusamy et al. |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0298820 A1 | 11/2012 | Manolidis |
| 2012/0302863 A1 | 11/2012 | Colin |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | Cormac |
| 2013/0150674 A1 | 6/2013 | Haig et al. |
| 2013/0172676 A1 | 7/2013 | Levy et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2014/0066940 A1 | 3/2014 | Fang et al. |
| 2014/0074170 A1 | 3/2014 | Mertens et al. |
| 2014/0142584 A1 | 5/2014 | Sweeney |
| 2014/0148647 A1 | 5/2014 | Okazaki |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257489 A1 | 9/2014 | Warren et al. |
| 2014/0275799 A1 | 9/2014 | Schuele |
| 2014/0275801 A1 | 9/2014 | Menchaca et al. |
| 2014/0276840 A1 | 9/2014 | Richter et al. |
| 2014/0277204 A1 | 9/2014 | Sandhu |
| 2014/0318582 A1 | 10/2014 | Mowlai-Ashtiani |
| 2014/0324044 A1 | 10/2014 | Haufe et al. |
| 2014/0336670 A1 | 11/2014 | Brabrand et al. |
| 2014/0357945 A1 | 12/2014 | Duckworth |
| 2014/0371537 A1 | 12/2014 | Marczyk et al. |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2018/0310975 A1 | 11/2018 | Haufe et al. |
| 2018/0368861 A1 | 12/2018 | Garcia-Bengochea et al. |
| 2020/0297378 A1 | 9/2020 | Hawkins et al. |

FOREIGN PATENT DOCUMENTS

| | | |
|---|---|---|
| JP | 2010500059 A | 1/2010 |
| WO | 2010089486 A2 | 8/2010 |
| WO | 2016111373 A1 | 7/2016 |
| WO | 2016131077 A1 | 8/2016 |
| WO | 2016168673 A1 | 10/2016 |

(56) References Cited

FOREIGN PATENT DOCUMENTS

| WO | 2017006684 A1 | 1/2017 |
| WO | 2017015480 A1 | 1/2017 |
| WO | 2017083648 A1 | 5/2017 |

OTHER PUBLICATIONS

International Search Report and Written Opinion for Application No. PCT/US2015/048485, dated Feb. 9, 2016. (16 pages).
International Search Report and Written Opinion for Application No. PCT/US2015/060978, dated Feb. 15, 2016 (8 pages).
Invitation to Pay Additional Fees for Application No. PCT/US2016/050022, mailed Nov. 3, 2016 (2 pages).
International Search Report and Written Opinion for Application No. PCT/US2016/050022, dated Feb. 1, 2017 (19 pages).
International Search Report and Written Opinion for Application No. PCT/EP2020/057404, dated Aug. 3, 2020 (19 pages).
Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Jung, K., et al., "A hands-free region-of-interest selection interface for solo surgery with a wide-angle endoscope: preclinical proof of concept," Surg Endosc, 2017, v. 31, pp. 974-980.
Communication Pursuant to Rule 164(2)(b) for Application No. EP 2071237.4 dated Dec. 20, 2023 (4 pages).
Japanese Search Report for Application No. 2021556773 dated Nov. 22, 2023 (23 pages).
Japanese Notice of Reasons for Refusal for Application No. 2021556773 dated Nov. 28, 2023 (11 pages).
Chinese Office Action for Application No. CN202080023251.5 dated Dec. 29, 2023 (12 pages).

* cited by examiner

SKIN FOUNDATION ACCESS PORTAL

CROSS-REFERENCE TO RELATED APPLICATIONS

This application is a continuation of U.S. application Ser. No. 16/362,488, filed Mar. 22, 2019, which is incorporated herein by reference in its entirety.

FIELD

Surgical access stabilization devices and related methods are disclosed herein, e.g., for stabilizing a port or other surgical access device relative to a patient during a surgical procedure.

BACKGROUND

There are many instances in which it may be desirable to stabilize an instrument or object. In surgical applications, for example, it can be desirable to stabilize a surgical access device, such as, for example, a port, relative to a patient during a surgical procedure. By way of further example, it can be desirable to establish, stabilize, and maintain a desired trajectory of the surgical access device during a surgical procedure to accommodate instruments, objects (e.g., implants), and the like that are passed percutaneously through the access device to a surgical site. Furthermore, it can be desirable to stabilize a surgical access device in a manner that minimizes interference with a surgical procedure and allows for easy and quick adjustment of the surgical access device to a different position, if necessary, during a procedure.

In current practice, a surgical instrument or object is commonly stabilized by connection or linkage to another instrument or object. Often, rigid connectors are used to stabilize a surgical instrument by connecting or linking it to a support. For example, a mechanical arm connector can be used to connect a surgical access device to a support, such as a surgical bed or a rigid implant post, to stabilize the access device during a surgical procedure. The stabilization methods and devices of the prior art rely on at least one additional stationary object at or near a surgical site to link to a surgical access device. Such systems can be especially burdensome in a minimally invasive surgical procedure, where the size of an operating area is small with only a limited amount of space for maneuvering.

Furthermore, use of a rigid mechanical arm connector to stabilize a surgical access device constrains a surgical procedure in several ways. For example, the location of a support (e.g., a surgical table or a rigid implant post) dictates a location of the access device based on the dimensions and configuration of the mechanical connector. Similarly, rigid mechanical connectors of the prior art can restrict a range of access device movement once connected to a support. Often, surgeons desire a greater range of motion during a surgical procedure in at least one preferred direction based on the anatomy of the procedure. For example, in a spinal procedure surgeons often want the ability to achieve greater port movement in a direction transverse to the spinal column. Rigid connectors prevent this desired movement, due to physical constraints of the connector and accompanying support structure(s). Moreover, the flow of a surgical procedure can be dictated by the connector stabilization systems of the prior art rather than a function of a surgeon's expertise. For example, where a surgical access device is stabilized by connection to a pedicle screw or other implant post, contralateral screws must first be placed in the patient prior to insertion and stabilization of the access device.

Accordingly, there remains a need for devices and techniques for establishing, stabilizing, and maintaining a desired trajectory and positioning of a surgical instrument, in particular a surgical access device, during a surgical procedure in an easier, less constrained manner.

SUMMARY

The present invention generally provides devices and methods for stabilizing a surgical access device. In particular, a surgical access device, such as a port, can be stabilized within a surgical incision relative to an anchor surface, e.g., a patient's skin, using the devices and methods described herein. In one aspect of the invention, a surgical access stabilization device is provided that includes a pad having a proximal facing surface and an adhesive distal facing surface, a surgical access device coupled to the pad, and a locking mechanism to selectively lock a position of the surgical access device with respect to the pad.

The surgical access stabilization device described above can have a variety of modifications that are within the scope of the invention. For example, in some embodiments, the pad can have an opening extending therethrough to receive the locking mechanism. Further, in some embodiments, the opening can be an elongated slot. In some embodiments, the opening can be centrally located on the pad. The pad can further include imaging features to aid in imaging of the pad. In some embodiments, the pad can include navigational features to aid in navigation of the surgical access device. In certain embodiments, the pad can have a central portion with at least one radial finger. In some embodiments, the pad can be made from any of a flexible fabric, an elastomer, and a polymer.

In some embodiments, the locking mechanism can selectively lock translational movement of the surgical access device in a direction along the proximal facing surface of the pad. In some embodiments, the locking mechanism can selectively lock translational movement of the surgical access device in a direction transverse to the proximal facing surface of the pad. Still further, in some embodiments, the locking mechanism can selectively lock any of rotational movement of the surgical access device and angular movement of the surgical access device. The locking mechanism of the present invention can take a variety of forms. For example, in some embodiments, the locking mechanism can include at least one locking ring. While in other embodiments, the locking mechanism can include any of a releasable adhesive and a hook and loop fastener.

In another aspect, a surgical access stabilization system is provided that includes a pad having a proximal facing surface and an adhesive distal facing surface, a surgical access device that defines a working channel, and a connecting mechanism coupled between the pad and the surgical access device to place the surgical access device at a location remote from the pad.

The surgical access stabilization system described above can have a variety of modifications that are within the scope of the invention. For example, in some embodiments, the connecting mechanism can include an arm coupled at a first end to the surgical access device and coupled at a second end to the pad. Further, in some embodiments, the arm can be bendable to adjust placement of the first end relative to the second end.

In yet another aspect, a method of stabilizing a surgical access device is provided that includes making an incision in a patient, adhering a pad to the patient, inserting the surgical access device through the incision in the patient, coupling the surgical access device to the pad, and selectively locking a position of the surgical access device with respect to the pad.

The surgical access stabilization method described above can have a variety of modifications that are within the scope of the invention. For example, in some embodiments, the method can further include positioning the surgical access device within the incision by at least one of translating, rotating, and angulating the surgical access device relative to the pad.

In other embodiments, selectively locking the position of the surgical access device can prevent further translation, rotation, or angulation of the surgical access device with respect to the pad.

In some embodiments, the pad can be adhered to the patient after making the incision. In other embodiments, the pad can be adhered to the patient before making the incision. In certain embodiments, the pad can be adhered to the patient at a location remote from the incision.

In some embodiments, coupling the surgical access device to the pad can include positioning the surgical access device within an opening of the pad. In other embodiments, coupling the surgical access device to the pad can include linking the surgical access device to the pad with a connector arm.

In other embodiments, the surgical access device stabilization method can further include deploying at least a portion of the pad from the surgical access device after the surgical access device is inserted through the incision.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Still further, sizes and shapes of the devices, and the components thereof, can depend at least on the anatomy of the subject in which the devices will be used, the size and shape of components with which the devices will be used, and the methods and procedures in which the devices will be used.

While the illustrated embodiments and accompanying description make particular reference to application in a spinal surgery procedure, and, in particular, to minimally invasive spinal surgery, the devices, systems, and methods described herein are not limited to these applications. Rather, the devices, systems, and methods described can be utilized in various applications which require or benefit from stabilization of an object, and are particularly well suited for surgical applications to stabilize a surgical access device relative to a patient at one or more desired position, trajectory, or orientation over the course of a surgical procedure.

FIGS. 1-4 illustrate a first exemplary embodiment of a surgical access stabilization device 100. The device 100 can be used to stabilize a surgical access device, e.g., a port or access device 10, inserted through an incision in a patient. Preferably, a surgical access stabilization device of the present invention can be patient-mounted to stabilize a surgical access device with respect to the patient. The device 100 can selectively restrict any one of translational, rotational, or angular movement of a port with respect to the patient. Furthermore, the surgical access stabilization device 100 can be used to establish, stabilize, and maintain the surgical access device at a desired trajectory during a surgical procedure and provide for easy adjustment as needed.

Figure 1:
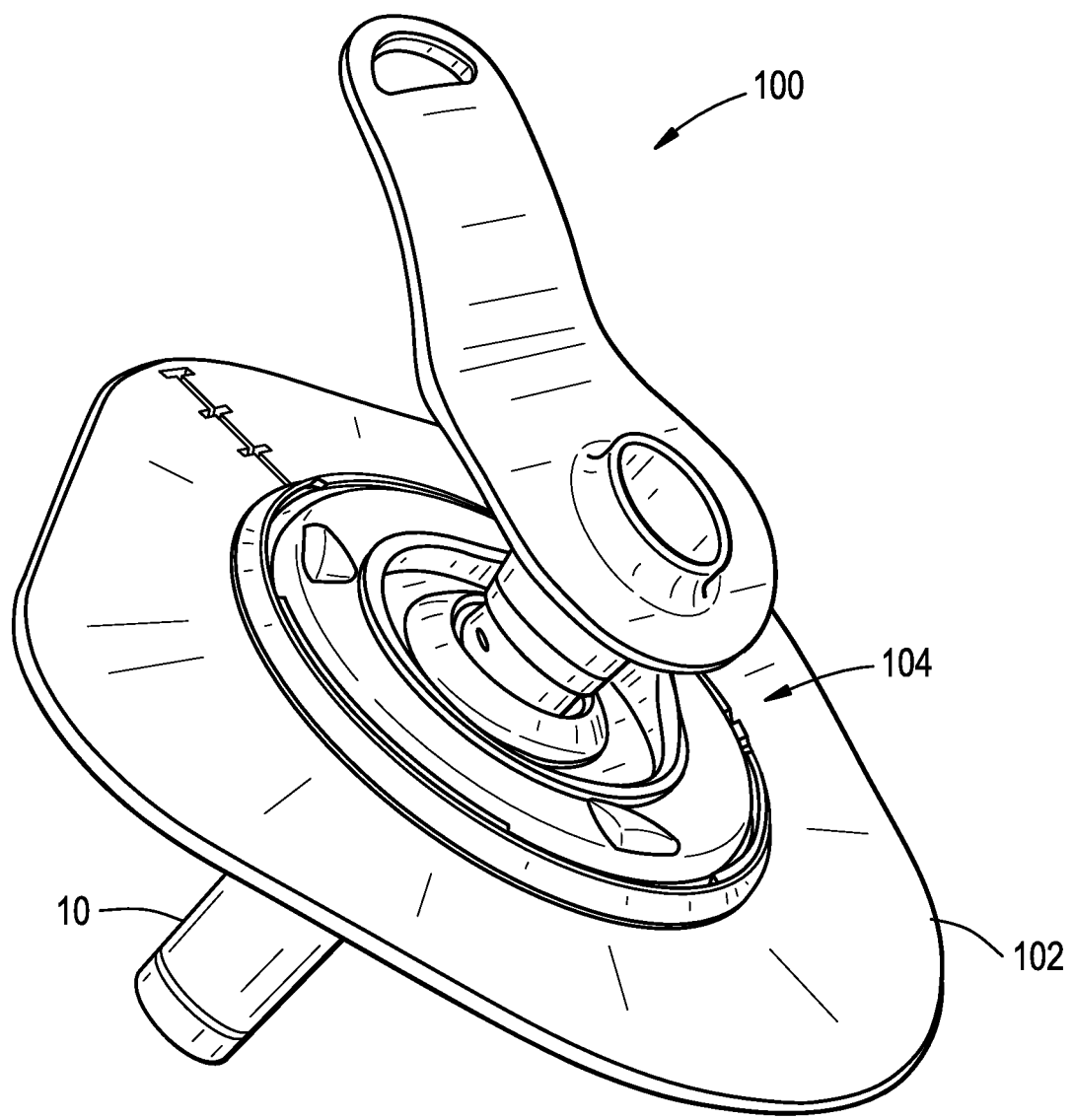
FIG. 1 is a perspective view of one embodiment of a surgical access stabilization device having a foundation pad and a locking mechanism with a surgical access device disposed therein.

FIG. 1 illustrates a preferred embodiment of a surgical access stabilization device according to the present invention. The surgical access stabilization device 100 is shown with a surgical access device, e.g., a port or access device 10, engaged therein. The surgical access stabilization device 100 can include a foundation pad 102 and a locking mechanism 104, described in greater detail below. Locking mechanism 104 can be configured to couple and secure port 10 to the pad 102. The locking mechanism can further be configured to facilitate positioning and adjustment of port 10 and can selectively lock movement of the port relative to the pad. Pad 102 can have an adhesive distal facing surface that is configured to contact and adhere to an anchor surface. In a preferred embodiment, an anchor surface can be the skin of a patient and a distal facing surface of the pad can be a patient contacting surface. A proximal facing surface of the pad can be exposed to a user and can include features to facilitate placement of the pad and adjustment of the port 10 during a surgical procedure.

Figure 2:
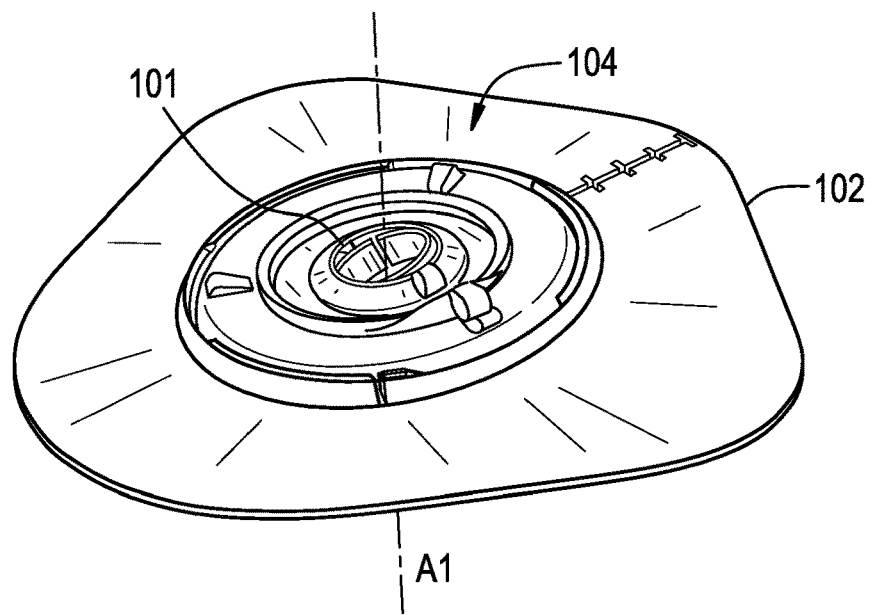
FIG. 2 is a perspective view of the surgical access stabilization device of FIG. 1.
Figure 3:
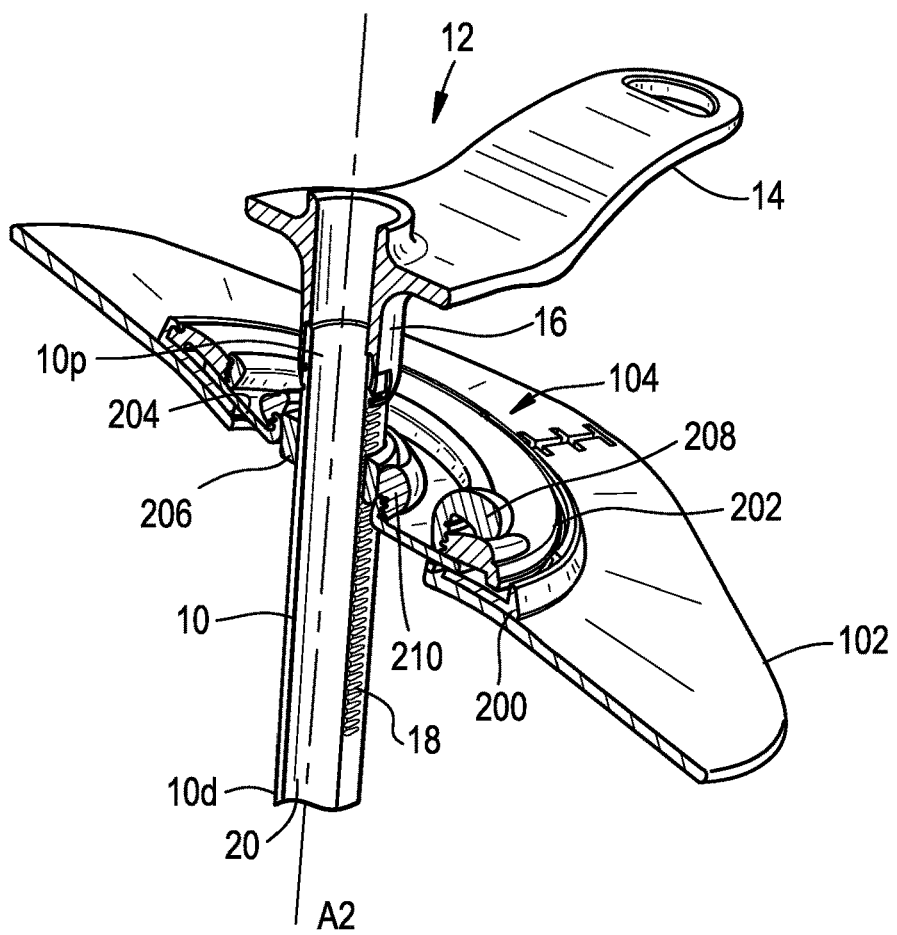
FIG. 3 is a cross sectional view of the surgical access stabilization device of FIG. 1 with a surgical access device disposed therein.

FIG. 2 shows the surgical access stabilization device of FIG. 1 without a surgical access device disposed therein. A central opening 101 can extend through the surgical access stabilization device 100 and can be configured to receive the port 10. As shown in FIG. 2, in some embodiments, central opening 101 can extend through the locking mechanism 104 and the pad 102. A central axis A1 of the surgical access stabilization device can extend through the central opening 101 normal to the proximal surface of the pad. The port 10 can be inserted distally along the axis A1 through the central opening 101 such that the port 10 is received within the surgical access stabilization device. FIG. 3 illustrates a cross-sectional view of FIG. 1, showing the surgical access stabilization device 100 with port 10 inserted through central opening 101. Here, the various components making up one embodiment of a locking mechanism 104 can be seen in an assembled configuration. In one embodiment, locking mechanism 104 can include a base 200, a retaining ring 202, a skirt 204, a split ring 206, a first locking piece 208, and a second locking piece 210, each of which will be described in greater detail with reference to additional figures below.

Figure 4:
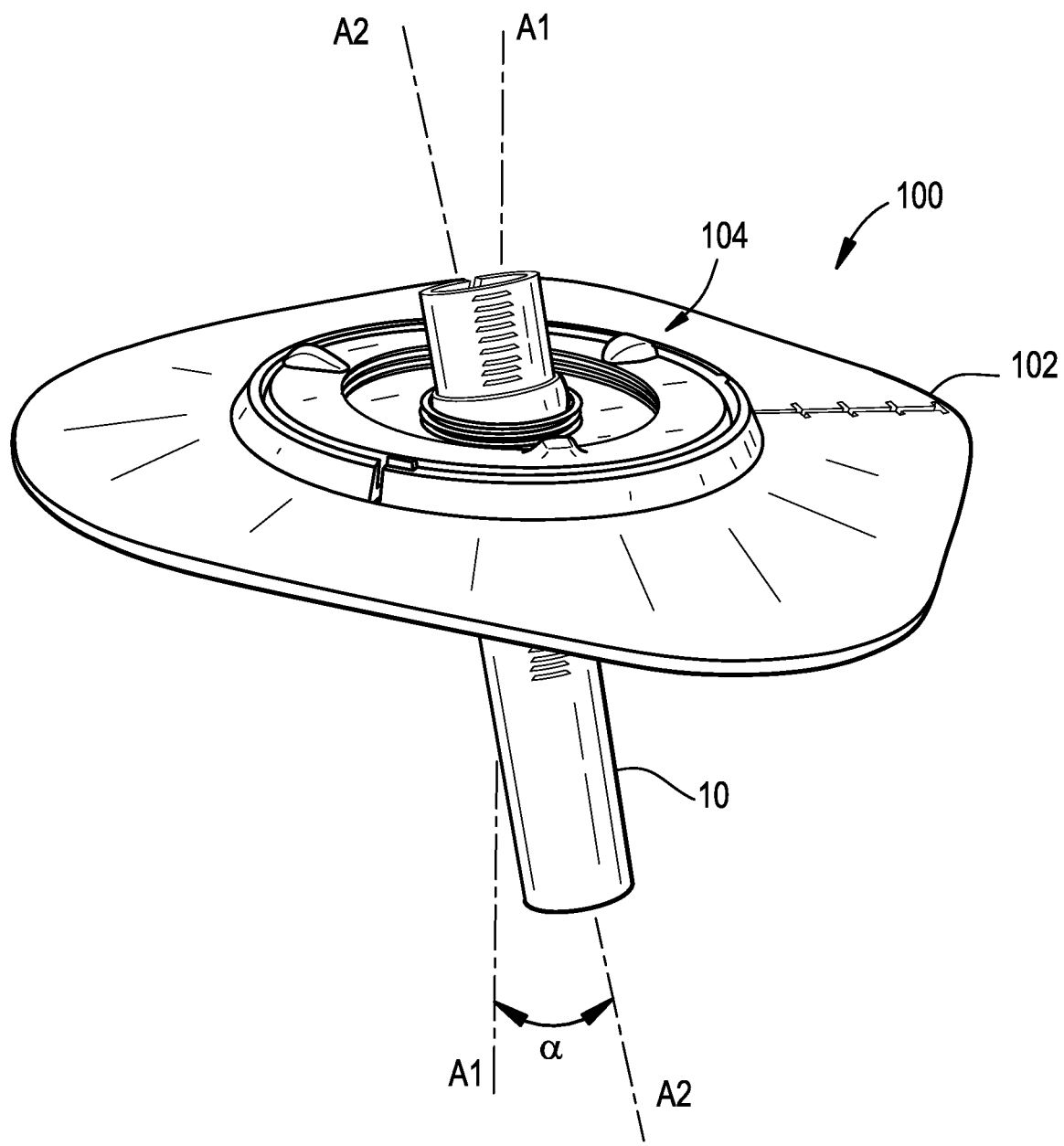
FIG. 4 is a perspective view of the surgical access stabilization device of FIG. 1 with a surgical access device disposed therein.

The port 10 can have a proximal end 10p and a distal end 10d with an inner lumen 20 extending therebetween having a longitudinal axis A2. When port 10 is inserted into surgical access stabilization device 100, the proximal end 10p of port 10 can remain proximal to the surgical access stabilization device, while the distal end 10d of port 10 can extend distally beyond the surgical access stabilization device to a surgical site through an incision in a patient. It will be appreciated that in the orientation shown in FIG. 1 and FIG. 3, the longitudinal axis A1 of the surgical access stabilization device and the port axis A2 are collinear as a result of the depicted orientation of the port 10 with respect to the surgical access device 100. More specifically, the port 10 is shown inserted in the surgical access device 100 without any angulation relative to the pad 102, such that the port axis A2 is aligned with the longitudinal axis A1 of the surgical access device 100. As the port 10 is angled with respect to the surgical access device 100, the longitudinal port axis A2 can be offset or angled with respect to the longitudinal axis A1 of the surgical access stabilization device. This is because movement of the port 10 relative to pad 102 can adjust an angle between port axis A2 and stabilization device axis A1. For example, as can be seen in FIG. 4, port 10 can be angled within locking mechanism 104 relative to pad 102 such that the port axis A2 is moved an angle α from the longitudinal axis A1 of the surgical access stabilization device. It will be appreciated that an angle α of zero degrees corresponds to a collinear orientation of port 10 and the longitudinal axis of the surgical access stabilization device.

Turning back to FIG. 3, the port 10 can have a handle 12 to allow an operator to manipulate the port 10 within the surgical access stabilization device. The handle 12 can include a grip portion 14 and port extension portion 16. Port extension portion 16 can extend axially to engage with the proximal port end 10*p* such that an inner lumen of the port extension portion is aligned with port lumen 20. Extending lumen 20 by engaging handle 12 can facilitate easier insertion of instruments, implants and the like through inner lumen 20 of the port 10. In one embodiment, an outer surface of the port 10 can have engagement features 18 that are configured to mate with complementary engagement features of the handle 12 to secure the port in a desired longitudinal position. For example, an outer surface of the port 10 can have a plurality of longitudinally aligned grooves 18. In one embodiment, the port extension portion 16 of the handle 12 can have at least one inwardly extending protrusion configured to selectively engage with at least one of the grooves 18 of port 10. In this manner, the handle, by way of adjusting the engagement between the port extension portion and the plurality of grooves 18, can be placed at a desired position on port 10. One skilled in the art will appreciate that alternative engagement methods are available to engage the handle 12 with the port 10. With the handle 12 secured to the port 10, a grip 14 can be used to move the port 10 with respect to the pad 102 and the axis A1 in any of a rotational, angular, or translational direction. Alternatively, the proximal end of port 10*p* can be directly manipulated, without attaching a handle thereto, to facilitate movement of the port.

The grip portion 14 can extend in a direction substantially transverse to port axis A2 and can be configured to facilitate manipulation of the port by a user. The grip portion 14 can encompass any variety of geometries. In a one embodiment, depicted in FIGS. 1 and 3, the grip portion 14 can have a sloped lever shape with semi-circular ends. Preferably, the grip body can slope in a proximal direction. The grip portion 14 can be shaped to facilitate easy grip and manipulation by a user. For example, a sloped portion of grip portion 14 can have a profile that can comfortably receive a user's hand or fingers.

Figure 5:
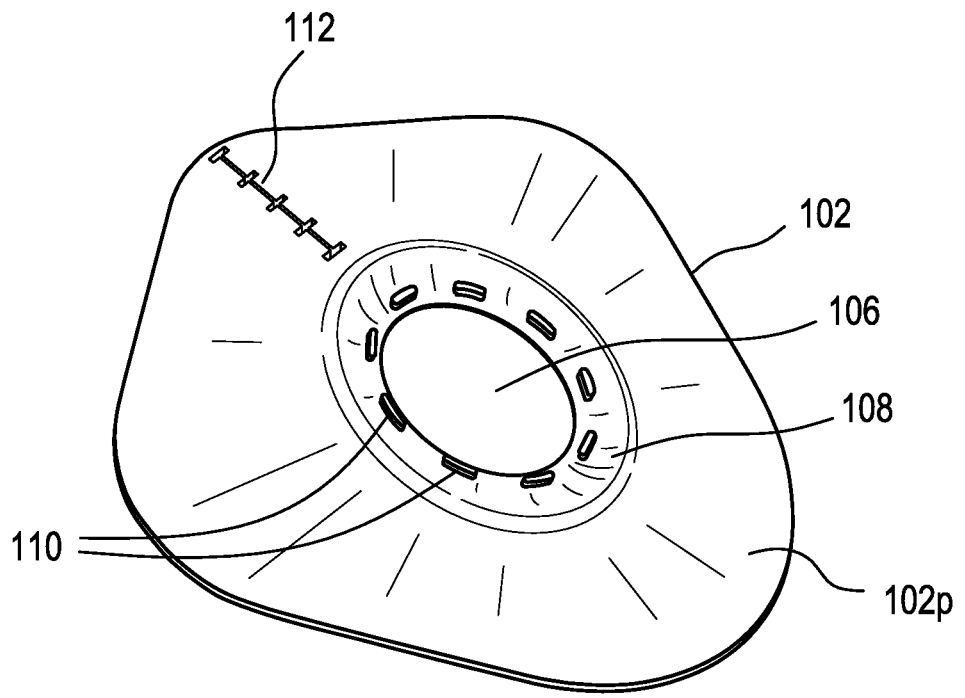
FIG. 5 is a perspective view of the foundation pad of FIG. 1.

FIGS. 5-25 illustrate various exemplary components of a stabilization device 100. FIG. 5 shows an exemplary embodiment of a foundation pad 102. The pad can have a proximal facing surface 102*p* and an adhesive distal facing surface, not shown. The adhesive distal facing surface can be adhered to an anchor surface such that the pad 102 is secured to the anchor surface. For example, the pad 102 can be adhered to the skin of the patient such that the pad 102 is securely anchored relative to the patient. In other embodiments, however, the pad 102 can be adhered to any variety of surfaces. The pad 102 can preferably be made from a flexible material such that the pad can closely contour to the anchor surface. A flexible pad 102 can allow the pad to contour intimately to a patient's skin at any of a variety of application locations. The adhesive distal facing side of pad 102 can have a distal adhesive layer. For example, the adhesive layer can be a medical grade adhesive.

By way of non-limiting example, the pad 102 can be made from any of a flexible fabric, an elastomer, and a polymer. Exemplary materials can include synthetic rubbers or natural rubbers. In one embodiment, the pad 102 can be made from a thin polymer, such as, for example, a rubber, neoprene, polytetrafluoroethylene (PTFE), etc. In some embodiments, a thin polymer pad can have a thickness of 1 mm to 5 mm. In other embodiments, a thin polymer pad can have a thickness of 1.5 mm to 3.5 mm.

The pad 102 can have any variety of sizes and shapes, and can be adjusted to particularly suit a surgical procedure or application. For example, the shape of a pad 102 can be configured to cover an entire sterile drape opening. In one embodiment, as shown in FIG. 5, the pad 102 can have a generally four sided shape with rounded corners. Alternatively, a pad can have a thin shape to contour into an anatomy, such as a waist, of a patient with a small stature. Further, the pad 102 can be cut, trimmed, or otherwise shaped to aid in placement for a particular application or surgical procedure. For example, pad 102 can be cut to conform to obstructions or objects that might be placed at or near a surgical site.

The pad 102 can have an opening 106 extending through the pad from the proximal facing surface 102*p* to the distal facing surface. It will be appreciated that the opening 106 can be any of a variety of different shapes and sizes. Additionally, the opening 106 can be placed at a variety of different locations on the pad 102. For example, opening 106 can be generally circular and located at a central portion of the pad 102, as shown in FIG. 5. Alternatively, the opening 106 can be located off-center or closer to an edge of the pad 102. The pad 102 can have a concave portion 108 surrounding the opening 106. The concave portion 108 can promote a smoother engagement and relative motion between a locking mechanism 104 and the pad 102. In one embodiment the concave portion 108 of the pad 102 can have a similar shape or curve as a distal facing portion of the locking mechanism 104, as will be discussed in greater detail herein.

The pad 102 can have one or more engagement features that are configured to removably attach the pad to a locking mechanism. In one embodiment, one or more protrusions 110 can extend proximally from the proximal facing surface of pad 102. Protrusions 110 can be configured to engage with a complementary portion or portions of the locking mechanism 104 to facilitate a secure connection between the pad 102 and the locking mechanism 104. In one embodiment, protrusions 110 can be generally rectangular or oval shaped and extend a distance above the proximal facing surface of pad 102. In one embodiment, the pad 102 can include a plurality of protrusions 110 spaced around a perimeter of opening 106. Any number of protrusions 110 can be formed on the pad 102 such that a locking mechanism 104 can be stably mated with pad 102. While protrusions 110 are shown located around the perimeter of opening 106, the protrusions 110 can be placed in any of a variety of locations on the pad 102. Those having ordinary skill in the art will recognize that other engagement features and methods can be used to secure a locking mechanism 104 to a pad 102. Non-limiting examples of engagement features include snap mechanisms, a lock-and-key mechanism, any variety of screws or other threaded features, etc.

The pad can further include various features to aid or assist a user. The pad can have imaging features to aid in imaging of the pad during positioning. For example, pad 102 can include radio-opaque markings 112 to aid in fluoroscope identification during positioning. The radio-opaque markings can be identified by an imaging system to provide accurate feedback with respect to placement of the pad 102. In one embodiment, markings 112 can aide in positioning a locking mechanism engaged within the pad 102 or an opening 106 of pad 102 a certain known distance off a midline of a patient. The pad 102 can include navigational features to aid in navigation of a surgical access device coupled to the pad. For example, a pad can have reflective fiducials or markers to aid in surgical navigation of the coupled surgical access device trajectory or axis placement.

Figure 6:
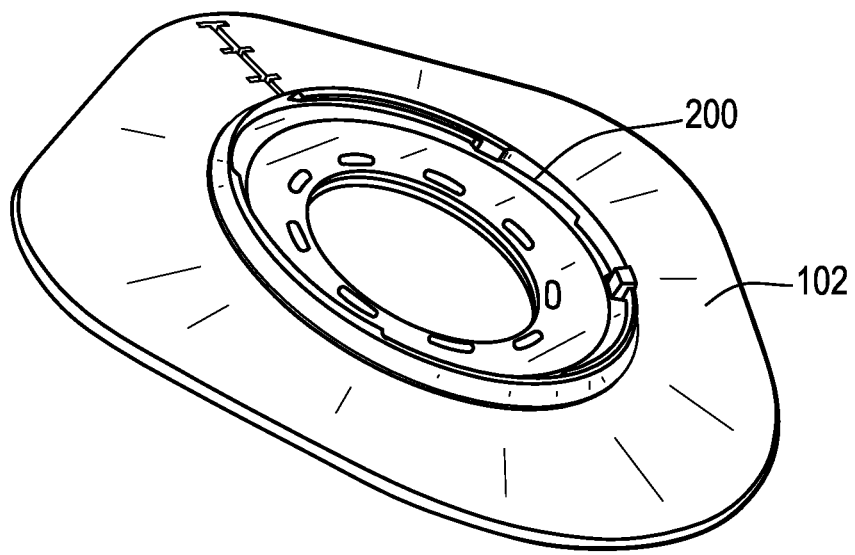
FIG. 6 is a perspective view of the pad with an engaged base portion of the locking mechanism of FIG. 1.

In one embodiment, locking mechanism 104 can be attached to pad 102 through opening 106 such that a portion of opening 106 and a central opening of locking mechanism 104 align to form central opening 101 of the surgical access stabilization device. In an exemplary embodiment, a base 200 of the locking mechanism 104 can be connected to pad 102, as shown in FIG. 6. The base 200 can serve as a primary contact between the locking mechanism 104 and the pad 102. Base 200 can include an opening 216 that can align with at least a portion of pad opening 106. While base 200 is depicted as having a generally ring shape, it will be appreciated that base 200 can have any variety of shapes. The base 200 and the pad 102 can be pre-assembled as a single unit prior to a surgical procedure. Alternatively, the pad 102 and the base 200 can be configured as two separate components that can be attached during a surgical procedure, either before or after adhering the pad 102 to an anchor surface. For example, pad 102 can be adhered to an anchor surface at a desired location. With the pad secured, engagement features of the base 200 can engage with engagement features of the pad 102, such that the base 200 is securely attached to the pad 102.

Figure 7:
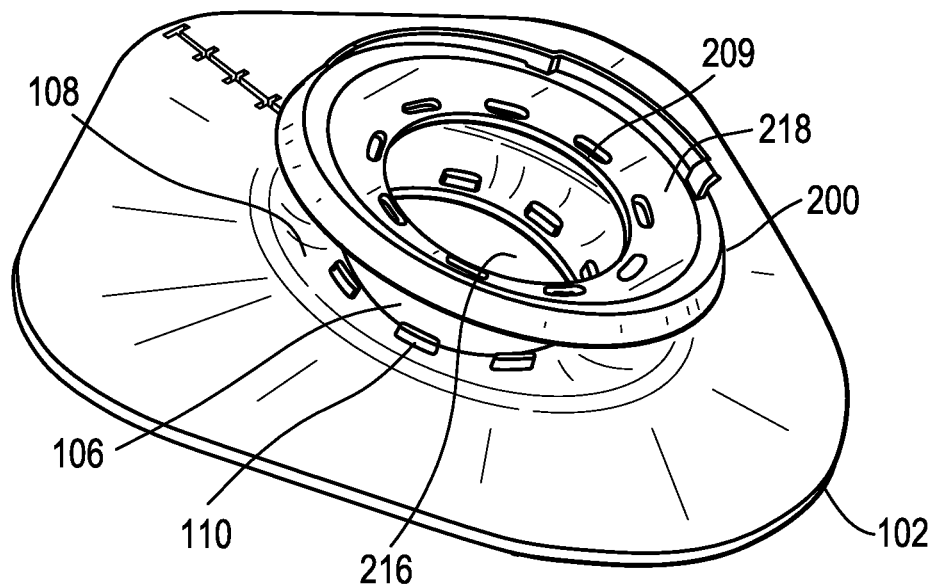
FIG. 7 is an exploded view of the foundation with the engaged base portion of FIG. 6.

By way of non-limiting example, as shown in FIG. 7, engagement features of the base 200 can be configured as slots 209. The slots 209 can extend through the base 200, and can be configured to receive the protrusions 110 of the pad 102. The base 200 can be securely attached to the pad 102 by placing the protrusions 110 of the pad within the slots 209 of the base to create a snap fit between the base and the pad. It will be appreciated that alternative attachment mechanisms are available to secure the base 200 to the pad 102. The base 200 can have a tapered portion 218 that extends from an outer portion of the base 200 inward to the opening 216. Preferably, the tapered portion 218 can have a geometry complementary to that of the concave portion 108 of the pad 102. When the base 200 is attached to the pad 102, the tapered portion 218 of the base 200 and the concave portion 108 of the pad 102 can be aligned to seat the base 200 within the pad 102.

Figure 8:
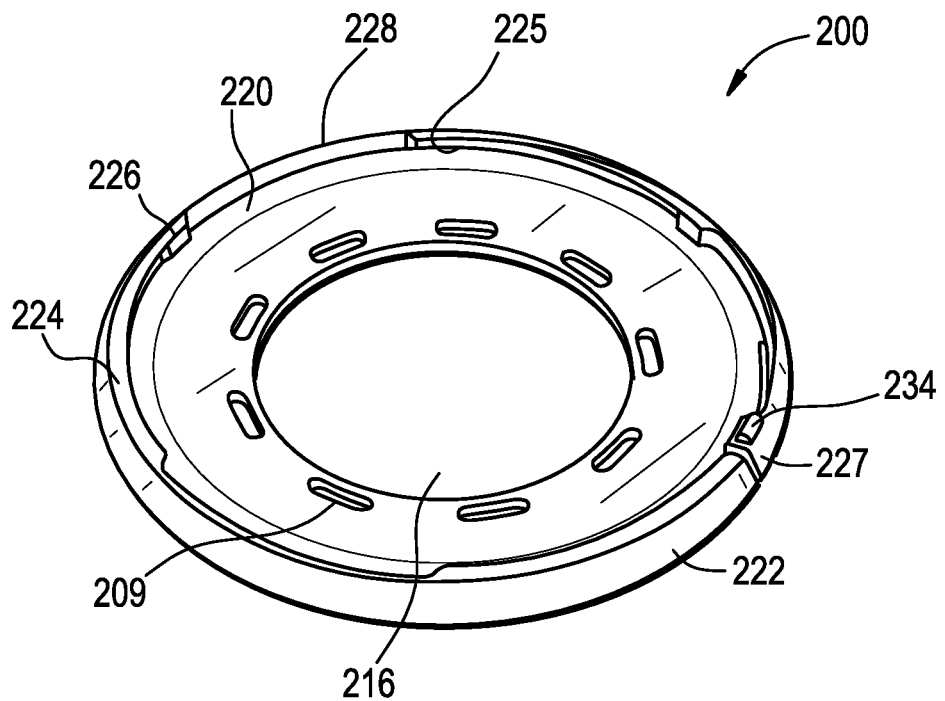
FIG. 8 is a perspective view of the base of FIG. 6.

FIG. 8 shows a perspective view of the base 200. A plateau 220 can be formed between the tapered portion 218 and an outer rim wall 222. Outer rim 222 can extend proximally from the plateau 220 creating a ring around the outer edge of the base. In one embodiment the outer rim 222 can taper from a distal end, at a junction with the plateau 220, to an opposing proximal end. Outer rim 222 can comprise one or more extension sections 224 having an upper lip at the proximal end of the rim 222 which extends radially inward over the plateau 220, such that a groove 225 is formed between the upper lip of the extension section 224 and a surface of the plateau 220. A transition 226 can be formed at one end of each extension section 224. In a preferred embodiment, the transition 226 can be formed at a far end of each extension section 224 as measured in a clockwise direction along a perimeter of the base 200. The transition 226 can be a solid portion that extends distally from the upper lip to the plateau 220. In other words, transition 226 forms a stop in circumferential groove 225. The transition 226 can also demarcate a transition between the extension section 224 and a recessed section 228. The recessed section 228 does not have any portion extending extend radially inward beyond the outer rim 222. As such, the transition 226 can have an outer edge that slopes from a radially inward position of the extension section 224 radially outward to a position at an inner surface of rim. The recessed section 228 can form a recess, or a pocketed area, between two extension sections 224.

Figure 9:
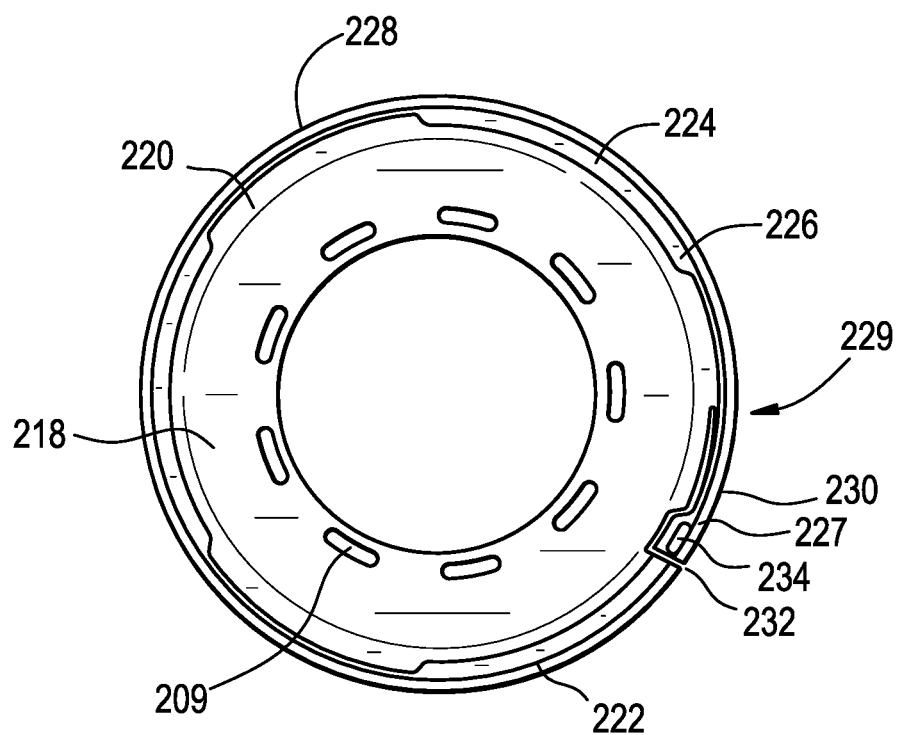
FIG. 9 is a top view of the base of FIG. 6.

As can be seen from a top view of the base 200 in FIG. 9, one embodiment of the base 200 can include three extension sections 224 separated by three recessed sections. Preferably, one of the recessed sections can be a modified recessed section 229. A tab portion 230 can be urged radially outward by an object inserted into the base 200 and rotated in a clockwise direction. The tab portion 230 can return to a neutral position, as shown in FIG. 9, once the outward force is removed. The tab portion 230 can be created by a channel 232 which extends radially inward from an outer edge of the rim 222, and continues a distance in a circumferential direction along the plateau 220. The tab portion 230 may be formed to include a stop 227 which, similar to the transition 226 described above, extends distally to the plateau 220. As will be discussed below, a retaining ring 202 can be rotatably received within base 200 such that the retaining ring can rotate between a locked and an unlocked state. The tab 230 can secure the retaining ring in the locked position, and prevent undesired rotation of the retaining ring back to the unlocked state. An identifying feature 234 can extend from a portion of the tab 230 to aid a user in orienting and assembling the surgical access stabilization device. For example, the identifying structure 234 can extend proximally from the stop 227 of tab portion 230. In one embodiment, to return the retaining ring from the locked state to the unlocked state, a user can locate the tab 230 by the identifying structure 234, and simultaneously urge the tab 230 outward by applying a force to the tab 230 and rotate the retaining ring 202 to the unlocked position.

Figure 10:
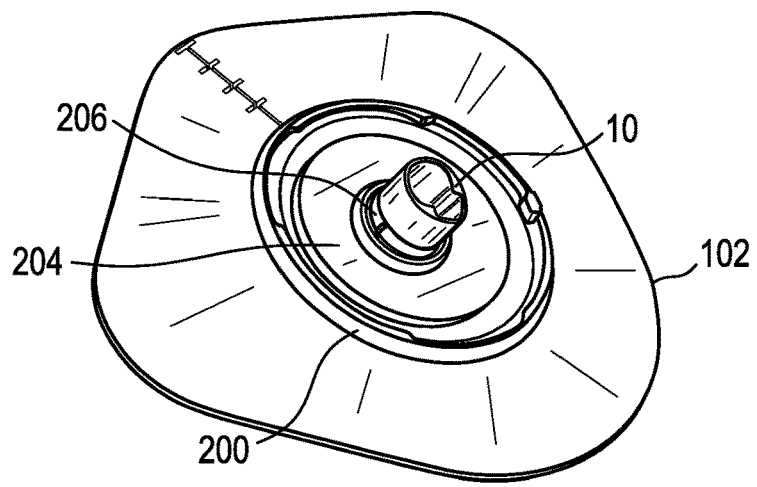
FIG. 10 is a perspective view of the foundation and the base, a skirt, and a split ring of the locking mechanism of the surgical access stabilization device of FIG. 1 with a surgical access device disposed therein.
Figure 11:
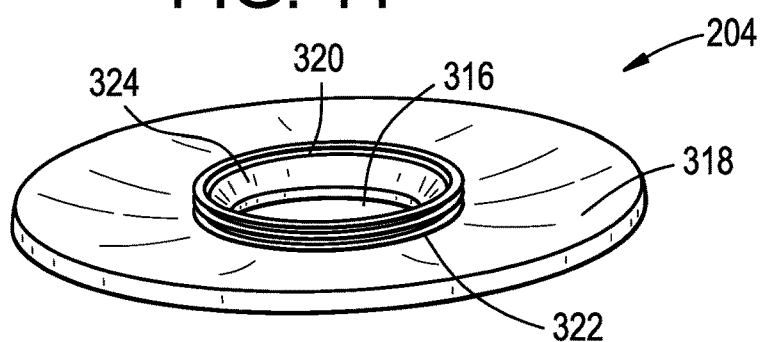
FIG. 11 is a perspective view of the skirt of FIG. 10.
Figure 15:
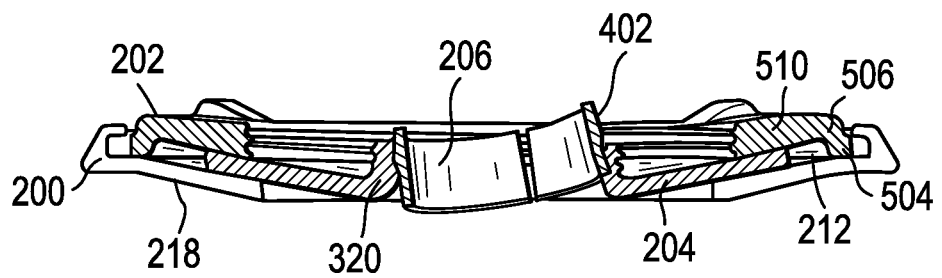
FIG. 15 is a cross sectional view of the locking mechanism components of FIG. 14.

Additional exemplary features of a locking mechanism 104 will now be described. FIG. 10 is a perspective view of the pad 102 with several components of the locking mechanism 104 coupling a port 10 to the pad. In addition to a base 200, FIG. 10 shows a skirt 204 and a split ring 206 of the locking mechanism 104. With the base 200 coupled to the pad 102, a skirt 204 can be placed atop a proximal facing surface of the base 200. As best shown in FIG. 11 and FIG. 15, the skirt 204 can preferably have a tapered surface 318. The surface 318 can have a complementary surface taper to the tapered surface 218 of the base 200. The skirt 204 can be placed such that the tapered surface 318 of the skirt 204 is seated within the tapered surface 218 of the base 200. The tapered surface 318 of skirt 204 can extend from an outer edge of the skirt 204 inward towards an opening 316. In one embodiment, the tapered surface 318 can be generally ring shaped and form a main body of the skirt 204. It will be appreciated that the skirt 204 can have any variety of shapes. When the skirt 204 is seated within the base 200, the opening 316 of the skirt 204 can align with at least a portion of the opening 216 of the base 200, and the opening 106 of the pad 102.

The skirt 204 can have an extension 320 extending proximally from the surface 318 to define the opening 316. In one embodiment, an inner surface 324 of the extension 320 defining the opening 316 can preferably be a smooth surface, tapered from a proximal end of the opening to a distal end of the opening. As will be described below, a smooth tapered surface 324 can facilitate rotational and angular movement of a split ring 206, and a surgical access device received therein, relative to the skirt 204. The extension 320 can include an engagement feature configured to engage with another portion of the locking mechanism 104, and preferably with a locking piece of the locking mechanism 104. In one embodiment, the engagement feature can be external threads 322 formed on an outer surface of extension 320. Other means for engaging the skirt 204 to a locking piece of the locking mechanism 104 are also considered within the scope of the invention.

The skirt 204 can preferably be made from a polymer or other flexible material. Skirt 204 is configured such that the skirt can translate in accordance with translational motion of a surgical access device received by the surgical access stabilization device 100. A thickness of the skirt 204 can preferably be slightly less than a height of a cavity formed between the base 200 and retaining ring 202. As will be described in detail below, an outer portion of skirt 204 can be slidably received in the cavity such that skirt 204 can translate in any radial direction along base 200.

Figure 12:
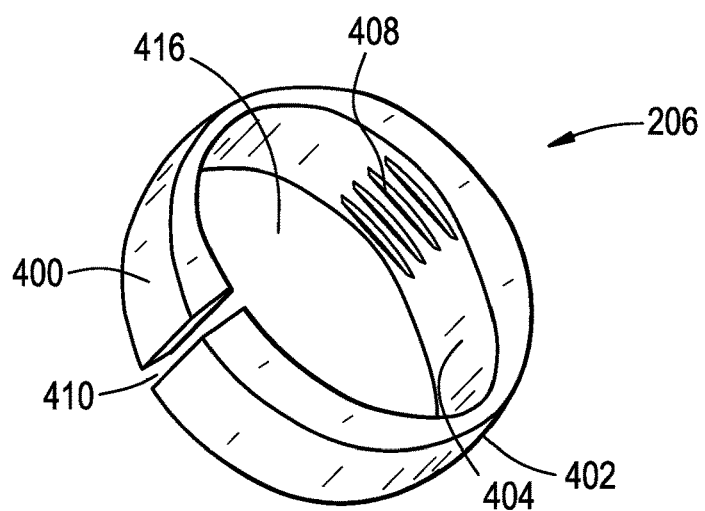
FIG. 12 is a perspective view of the split ring of FIG. 10.
Figure 13:
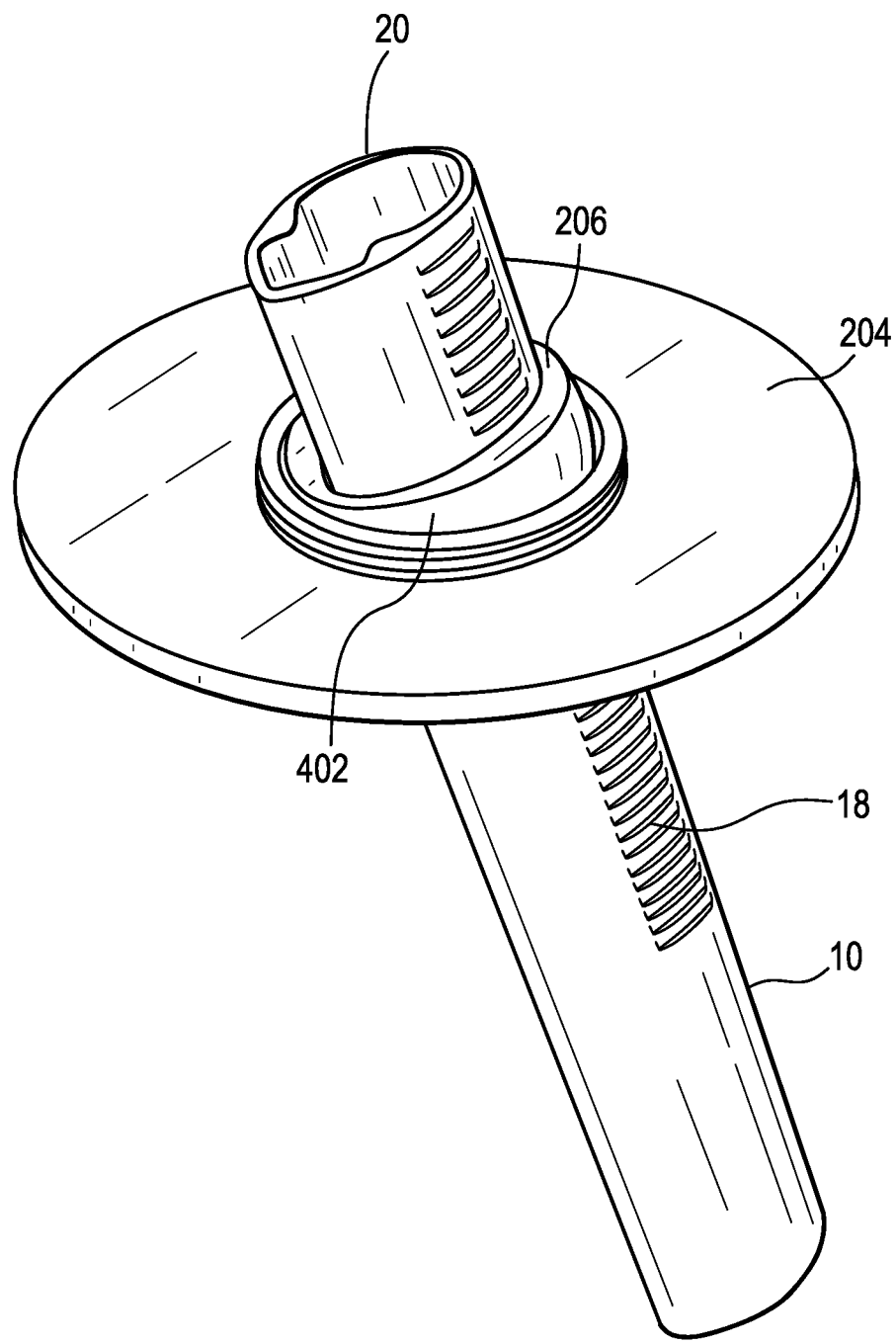
FIG. 13 is a perspective view of a skirt and a split ring of the locking mechanism of FIG. 1 with a surgical access device disposed therein.

FIG. 12 illustrates a split ring 206, which can be received within the opening 316 of the skirt 204 to facilitate coupling of a surgical access device by the locking mechanism 104 to the pad 102. The split ring 206 can have an opening 416 configured to receive a surgical access device. The opening 416 can be defined by a perimeter wall 400 having an outer surface 402 and an inner surface 404. In one embodiment the outer surface 402 and the inner surface 404 can have different shapes such that the perimeter wall 400 has a non-uniform thickness. By way of non-limiting example, the outer surface 402 can be generally circular, and the inner surface 404 can be an oval or an egg shape. In a preferred embodiment, the inner surface can have a perimeter that corresponds to a shape of a surgical access device to be received therein. The outer surface 402 of the split ring 206 can have a curved profile, while the inner surface 404 can have a linear profile. A curved profile of the outer surface 402 can allow the split ring 206 to move more easily relative to the skirt opening 316. In this manner, the split ring 206 can be rotated or angled relative to the skirt and the longitudinal axis A1 of the surgical access stabilization device. FIG. 13 illustrates a skirt 204 with a split ring 206 having a port 10 received through opening 416 of the split ring. As can be seen, the port has an egg shaped outer surface that is reflected by a shape of the inner surface 404 of the split ring 206.

Turning back to FIG. 12, a channel 410 can be formed extending through the perimeter wall 400. The channel 410 can provide flexibility to the split ring 206 such that the split ring can expand to accommodate a greater number of surgical access devices within the opening 416. The split ring 206 can have one or more engagement features configured to aid in a selective longitudinal positioning of a surgical access device 10 received in the opening 416. In one embodiment, at least one inwardly projecting protrusion 408 can be formed on the inner surface 404 to engage with complementary features formed on an outer surface of a surgical access device, such as a plurality of grooves 18. When a surgical access device passes distally through the opening 416, interaction of the split ring engagement features and complementary features formed on an outer surface of the surgical access device can provide for easier alignment and longitudinal adjustment of the surgical access device relative to the inner ring. Engaging engagement features of the split ring 206 with an inserted surgical access device can provide a secure connection between the two components, such that the split ring 206 can move in accordance with application of a force to the surgical access device. Additionally, complementary engagement features of a split ring and a surgical access device can provide beneficial tactile feedback to a user regarding alignment and engagement of a surgical access device with the inner ring.

Figure 14:
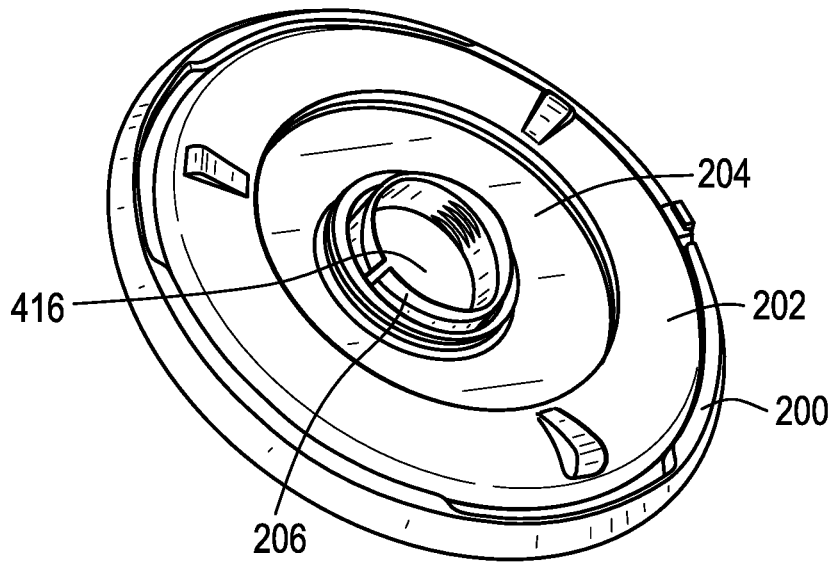
FIG. 14 is a perspective view of the base, the skirt, the split ring and a retaining ring of the locking mechanism of FIG. 1.

FIG. 14 shows a perspective view of a locking mechanism including an assembled base 200, skirt 204, split ring 206, and retaining ring 202. As shown, the opening 416 of the split ring 206 can extend through the various components of the assembled locking mechanism. A cross sectional view of FIG. 15 illustrates how the various components of the locking mechanism 104 can be assembled relative to one another. The skirt 204 can be placed such that an outer portion of the skirt is slidably received in the cavity 212 formed between a proximal facing surface of the base 200 and the retaining ring 202. The skirt 204 can thus translate within the cavity 212 with a force applied by a user. The split ring 206 can be placed within the opening defined by the extension 320 of the skirt 204. As discussed above, an outer curved surface 402 of the split ring 206 can be rotatably received by the inner surface 324 of the extension 320. The split ring 206 can thus be angled or rotated through a full range of motion within the opening 316 of the skirt 204.

Figure 16:
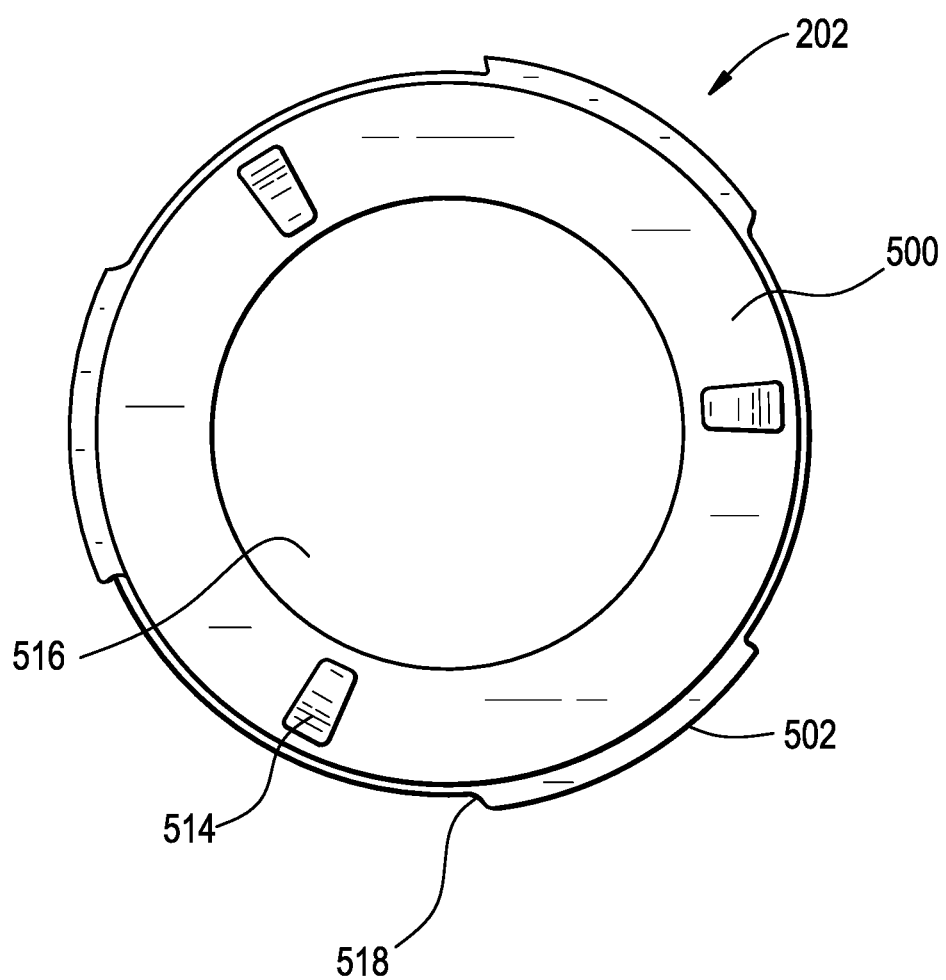
FIG. 16 is a top view of the retaining ring of FIG. 14.

The retaining ring 202 will now be described in greater detail with reference to FIGS. 15-19. FIG. 16 shows a top view of one embodiment of a retaining ring of the present invention. In one embodiment, the retaining ring 202 can have an annular main body 500 with a rim 504 having at least one radially extending protrusion 502. The retaining ring 202 can be configured such that the retaining ring can be placed and secured within the base 200. In one embodiment, the radially extending protrusions can engage with features of the base 200 to secure placement of the retaining ring in the base 200. The main body 500 can define an opening 516, at least a portion of which can align with other components of the locking mechanism to form the central pass-through opening 101. The retaining ring 202 can be sized such that the retaining ring fits within the base. Furthermore, the retaining ring main body 500 can extend radially inward at a distance removed from the surface of the base 200, forming a circumferential cavity 212 between the base 200 and the main body 500 configured to slidably receive the skirt 204. In on embodiment, the opening 516 can be generally circular and formed at a central location of the retaining ring 202. Preferably, the opening 516 can have a diameter that is greater than a diameter of opening 216 of the base 200 and greater than a diameter of the opening 316 of skirt 204.

The main body 500 can have a generally stepped profile formed from the outer rim 504, a proximally extending portion 506, and a laterally extending portion 510. The proximally extending portion 506 can extend proximally from the rim 504. As can be best seen in FIG. 15, the proximally extending portion 506 can form an outer circumferential ring of the main body 500 having a radial thickness that is less than a radial thickness of the main body 500. The laterally extending portion 510 can extend radially inward towards the opening 516 from a proximal end of the proximally extending portion 508. In particular, the laterally extending portion 510 can be raised a distance from a distal end of the proximally extending portion 508 such that the cavity 212 is formed beneath the laterally extending portion 510 from an inner radial point of the main body 500 radially outward to an inner facing surface of the proximally extending portion 506.

In other words, the main body 500, can have a solid wall circumference, i.e. proximally extending portion 508, and an overhang, i.e. laterally extending portion 510, which does not extend a full distal length of the solid wall circumference but rather creates a radial gap at a distal portion of the retaining ring 202. The laterally extending portion 510 can have a tapered profile such that a height of the laterally extending portion 510 increases along a radially inward direction. Preferably, the taper of the laterally extending portion 510 can be complementary to the tapered portion 218 of the base 200. In this manner, the radial cavity 212 formed between a distal facing surface of the laterally extending portion 510 and a proximal facing surface of the base 200, in particular a proximal facing surface of the tapered portion 218 of the base 200, can maintain a consistent height along a radial direction. Placing the retaining ring 202 within the base 200 creates the radial cavity 212. The components of the locking mechanism 104 can be sized such that the skirt 204 can fit slidably within the cavity 212.

A radially inward facing surface of the laterally extending portion 510 can have threads 512 configured to engage with another component of the locking mechanism 104. As will be described in detail below, the threads 512 can preferably engage with threads of a first locking piece 208. It will be appreciated that alternative engagement mechanisms between the retaining ring 202 and the first locking piece 208 are possible, so long as the first locking piece 208 can be selectively tightened or locked relative to the retaining ring 202.

Figure 17:
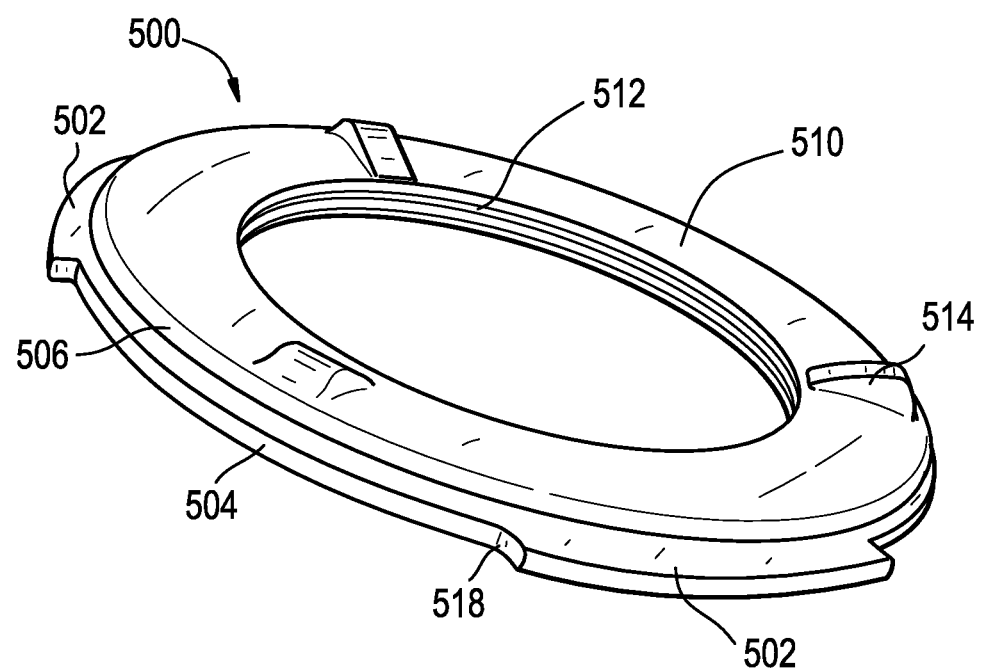
FIG. 17 is a perspective view of the retaining ring of FIG. 16.
Figure 18:
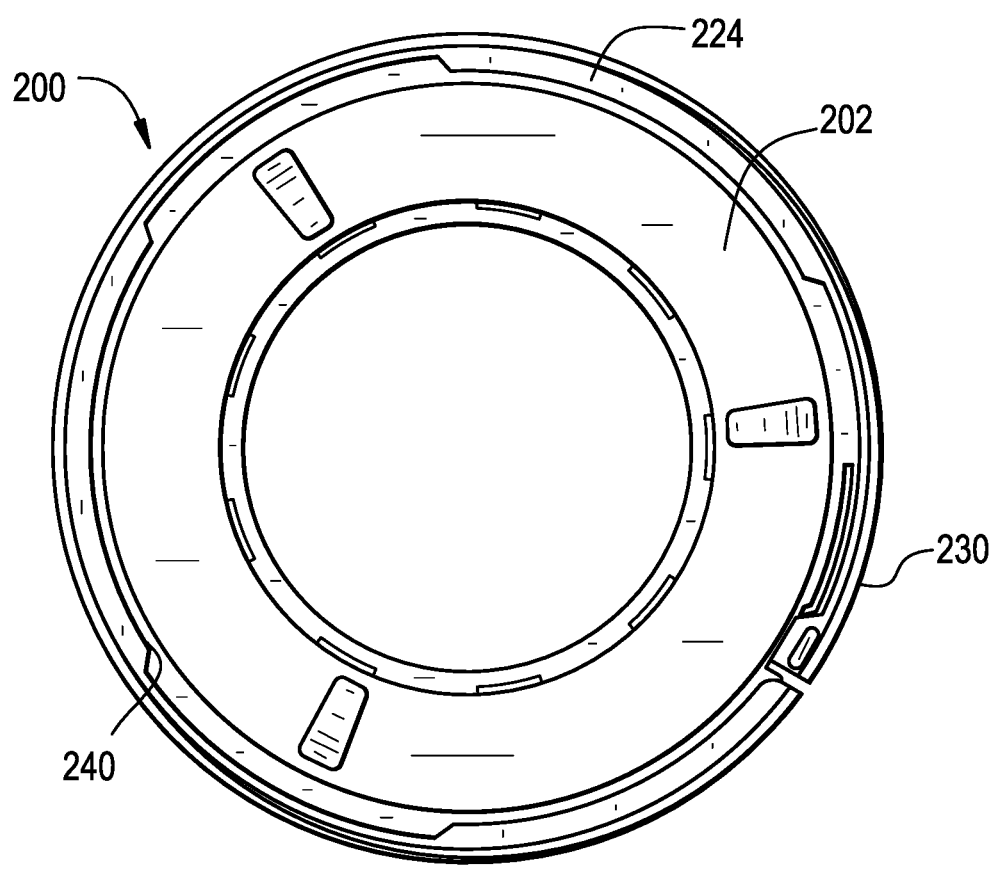
FIG. 18 is a top view of the retaining ring engaged with the base of the locking mechanism of FIG. 1.

With reference to FIG. 17, the radially extending protrusions 502 extend radially outward from the rim 504 and can be configured to engage with the groove 225 of the base 200. Inserting the retaining ring 202 within the base 200 can comprise aligning the radially extending protrusions 502 with the recessed sections 228 of the base 200 such that the protrusions 502 are aligned with the groove 225. Once inserted, the retaining ring 202 can be secured within the base 200 by rotating the retaining ring such that a leading edge 518 of a radially extending protrusion 502 abuts an edge of a transition 226 of the base 200. A proximal facing surface of main laterally extending portion 510 can have at least one protrusion 514 to aid a user in gripping and rotating the retaining ring 202 from a proximal facing surface. In this manner, the protrusion 502 can be housed within the extension portion 224. As seen in FIG. 18, the leading edge 518 and the transition 226 can have complementary geometry such that the leading edge 518 mates with the transition 226. With leading edge 518 abutting transition 226, the extension portion 224 of the base 200 extends over the radially extending protrusion 502 thereby restraining movement of the retaining ring 202 relative to the base 200 in a longitudinal direction. In a preferred embodiment, the extension portion 224 of the base 200 can extend a radial distance inward such that a small clearance 240 can be formed between an inner facing surface of the extension portion 224 and an outer facing surface of the main body 500.

Figure 19:
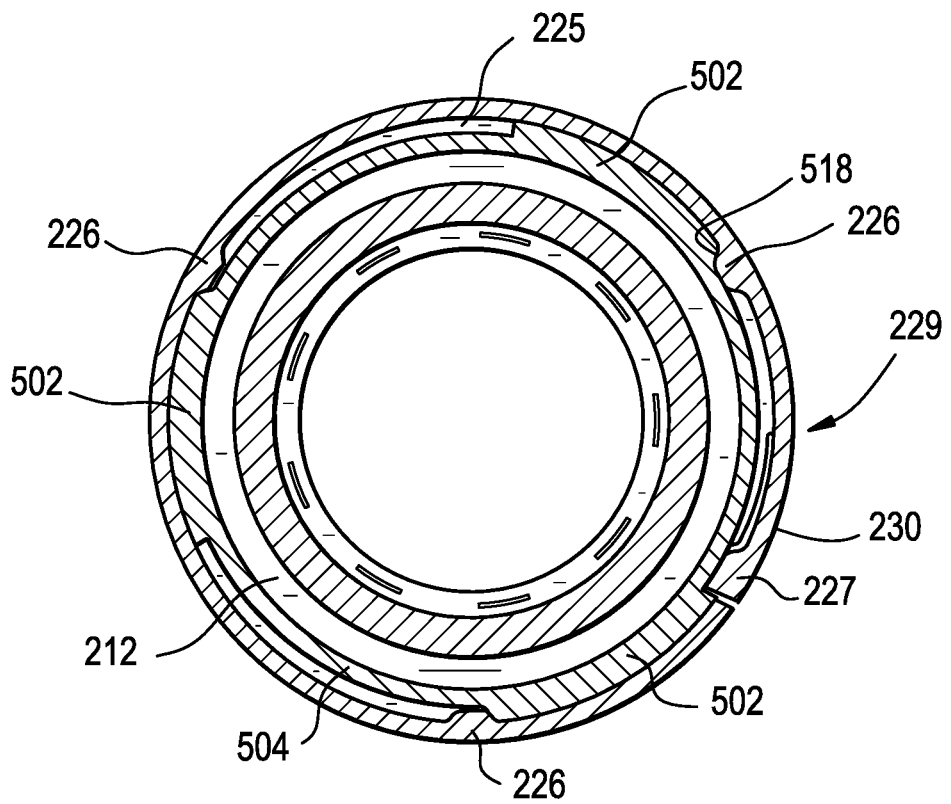
FIG. 19 is a cross sectional view of FIG. 19.

FIG. 19 is a cross sectional top view of FIG. 18, showing the retaining ring 202 engaged with the base 200 and rotated such that the protrusions 502 align with the extension sections 224. In this locked position, the leading edge 518 of each protrusion 502 can be seen abutting a transition 226 of the base 200. The cavity 212, configured to slidably receive the skirt 204, can be seen between an inner surface of the laterally extending portion 510 and the base 200.

Figure 20:
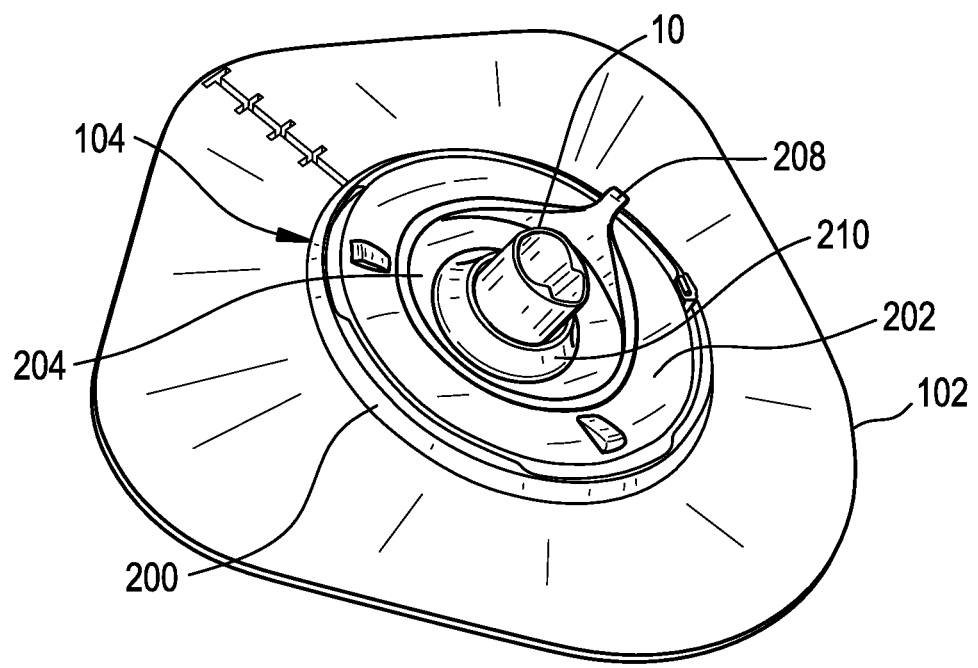
FIG. 20 is a perspective view of the surgical access stabilization device of FIG. 1 with a surgical access device disposed therein.

FIG. 20 shows the surgical access stabilization device 100 with a locking mechanism 104 having a first locking piece 208 and a second locking piece 210. In the illustrated embodiment, the locking mechanism 104 can include a first and a second locking piece to selectively lock a position of a surgical access device with respect to a foundation pad. In a preferred embodiment, the first and second locking pieces, e.g., 208 and 210, can be locking rings. In other embodiments, the locking mechanism 104 can include, for example, at least one releasable adhesive site, a threaded locking knob, or a lever action tightening wheel. It will be appreciated that any of the locking components disclosed herein are contemplated for use alone or in combination to selectively lock motion of a surgical access device relative to a pad. In an exemplary embodiment, as shown in the cross-sectional view of FIG. 21, the first locking piece 208 can be a locking ring configured to engage with the retaining ring 202 to selectively lock translation movement of an inserted surgical access device, such as port 10. The second locking piece 210 can be a locking ring configured to engage with the skirt 204 to selectively lock rotational, angular, and translational movement of a surgical access device, such as port 10, inserted within the split ring 206.

Figure 22:
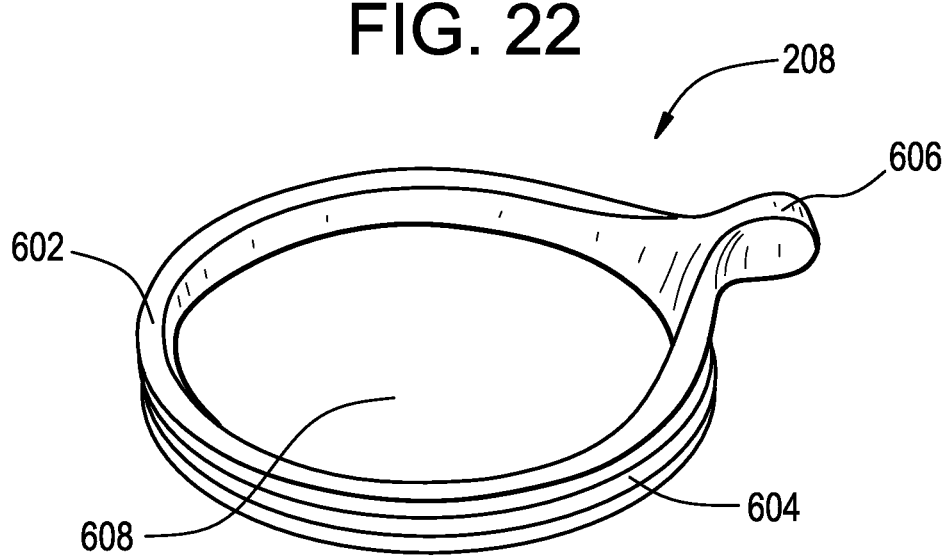
FIG. 22 is a perspective view of one embodiment of a first locking piece.

FIG. 22 shows a perspective view of an embodiment of the first locking piece 208. Preferably, in one embodiment, the first locking piece can be generally ring shaped having a wall 602 and an opening 608. An outer diameter of the first locking piece can preferably be substantially the same or slightly smaller than an inner diameter of the retaining ring 202. An outer surface of the wall 602 can have an engagement feature 604, configured to engage with a complementary engagement feature of the retaining ring 202. Preferably, the engagement feature can be threads 604 formed on the outer surface of wall the 602. A tab 606 can extend radially from an upper portion of the wall 602 to aid in rotating or otherwise moving first locking piece 208. In one embodiment, the tab 606 can be sized and shaped to facilitate a user grip of the tab 606 and rotation of the first locking piece 208.

Figure 21:
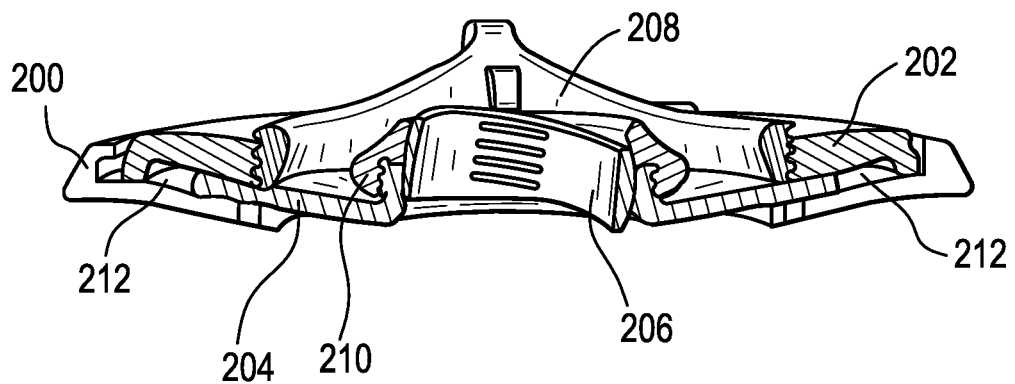
FIG. 21 is a cross sectional view of the locking mechanism of FIG. 20.

FIG. 21 shows a cross sectional view of the first and second locking pieces 208, 210 engaged with retaining ring 202 and skirt 204, respectively. Base 200 and split ring 206 are also shown. The first locking piece 208 can be rotated in a first direction relative to the retaining ring 202 to move the first locking piece 208 distally towards the base 200. The first locking piece 208 can be rotated in a second direction relative to the retaining ring 202 to move the first locking piece 208 proximally away from the base 200. As the first locking piece 208 moves distally towards the base 200, the skirt 204, placed within the cavity 212, can be clamped between the base 200 and the first locking piece 208 such that translational movement of the skirt 204 is restricted. On the other hand, as the first locking piece 208 is rotated in the second direction and moved proximally away from the base 200 along the inner circumference of the retaining ring 202, the compressive force on the skirt 204 can be released, allowing the skirt 204 to translate in any radial direction relative to the base 200. More particularly, a surgeon or user can apply a force to the skirt 204 such that an outer portion of the skirt 204 can move within the cavity 212 when the skirt 204 is not clamped by the first locking piece 208. In this configuration, motion of the skirt 204 is constrained by a radial depth of the cavity 212 and the size of skirt 204.

Figure 23:
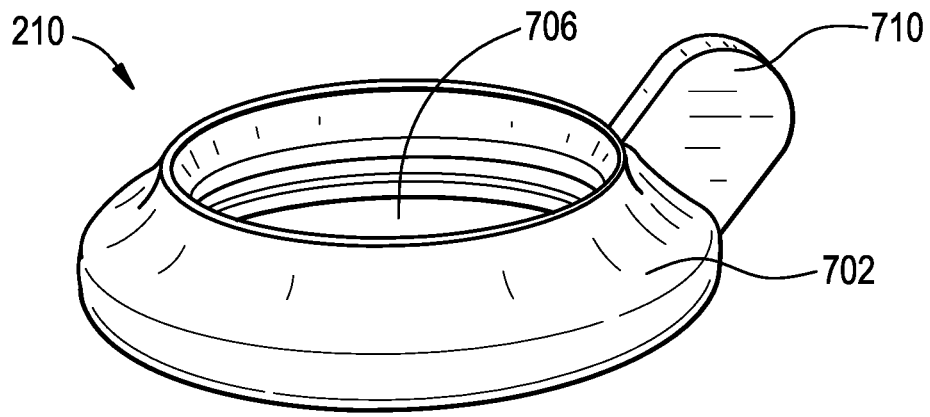
FIG. 23 is a perspective view of one embodiment of a second locking piece.
Figure 24:
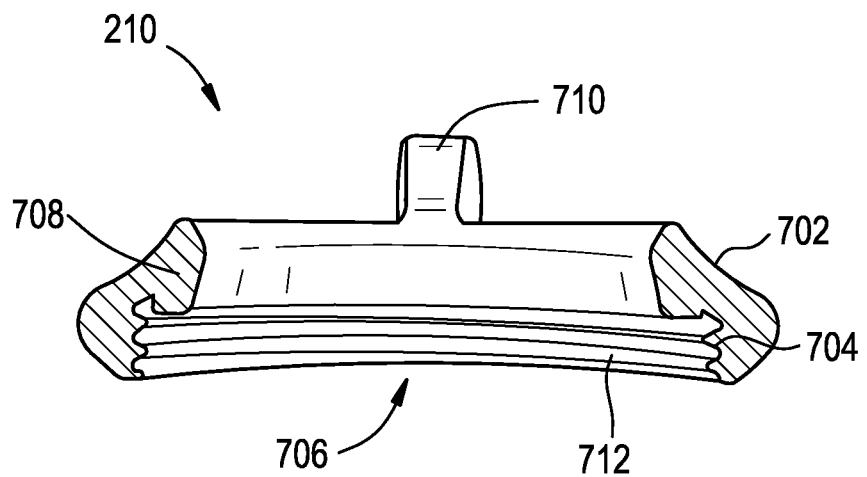
FIG. 24 is a cross sectional view of the second locking piece of FIG. 23.

FIG. 23 shows an exemplary embodiment of the second locking piece 210 configured as a locking ring formed by the wall 702 with a central opening 706. An outer surface of the wall 702 can be shaped to have a curved lower portion and a tapered upper portion. With reference to FIG. 24, the wall 702 can have a radially inward extending upper portion 708 that forms a hood over an inner surface 704 of the second locking piece 210. The opening 706 can be defined at a proximal end by an inner surface of the upper portion 708 and by the inner surface 704 at a distal end. In this manner, the opening 706 can have a first diameter at the proximal end that is smaller than a second diameter of the opening 706 at the distal end. As will be described in detail below, a larger diameter opening in the distal end of the opening 706 can allow for radial movement of an object, i.e. the extension 320 of the skirt 204, engaged with the second locking piece to selectively restrict motion of a surgical access device received within the surgical access stabilization device 100.

Preferably, the inner surface 704 can have an engagement feature 712 configured to engage with a complementary engagement feature of the skirt 204. In one embodiment, the second locking piece can have internal threads 712 formed along the inner surface 704 configured to engage with the threads 322 on the external surface of the skirt extension 320. The second locking piece 210 can be rotated in a first direction relative to the skirt 204 such that the second locking piece 210 moves distally relative to the skirt 204. The second locking piece 210 can be rotated in a second direction relative to the skirt 204, such that the second locking piece 210 moves proximally relative to the skirt 204. A tab 710 can extend proximally from an outer surface of the wall 702. Similar to the tab 606 of the first locking piece, the tab 710 can aid in rotation or movement of the second locking piece 210 by a user. Preferably, the tab 710 can be sized and shaped to facilitate a user grip of the tab 710.

Figure 25:
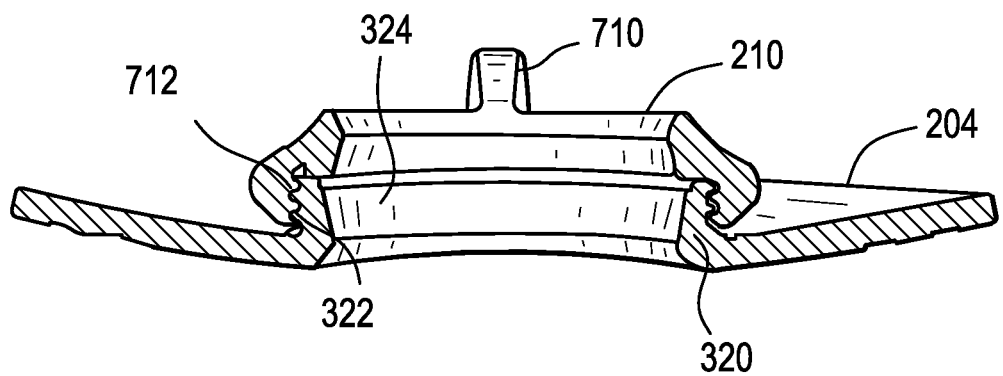
FIG. 25 is a cross sectional view of the second locking piece of FIG. 22 engaged with a skirt.

FIG. 25 shows a cross-sectional view of one embodiment of a second locking piece 210 engaged with a skirt 204. As can be seen, internal threads 712 of the second locking piece 210 can engage with external threads 322 of the extension 320 of the skirt 204. As the second locking piece 210 is rotated in the first direction causing the second locking piece 210 to move in a distal direction relative to the skirt 204, the second locking piece 210 can exert a compressive force in a radially inward direction such that the extension 320 of the skirt 204 is urged radially inward. On the other hand, when the second locking piece 210 is rotated in the second direction, the second locking piece moves proximally relative to the skirt, thereby reducing any inward compressive forces applied by the second locking piece on the skirt 204. In this manner, when a surgical access device is received within the opening formed by the skirt 204, the second locking piece can selectively restrict movement between the surgical access device and the skirt by selectively applying and removing an inward compressive force on the skirt extension 320. As can been seen from FIG. 25, the tapered inner surface 324, which defines the opening of the skirt 204, is tapered such that a radially inward compressive force can cause an upper portion of the tapered surface 324 to move radially inward towards a more linear profile, and abut against an outer surface of an instrument or object received therein. In an exemplary embodiment, and with reference back to FIG. 21, the split ring 206 can be held within the tapered surface 324 to receive a surgical access device. A radial compressive force imparted on the skirt extension 320 by the second locking piece 210 can cause the extension 320 to compress inwardly against the split ring 206. This inward compression can restrict motion of the split ring 206, and thus motion of the received surgical access device, relative to the skirt 204.

Figure 26:
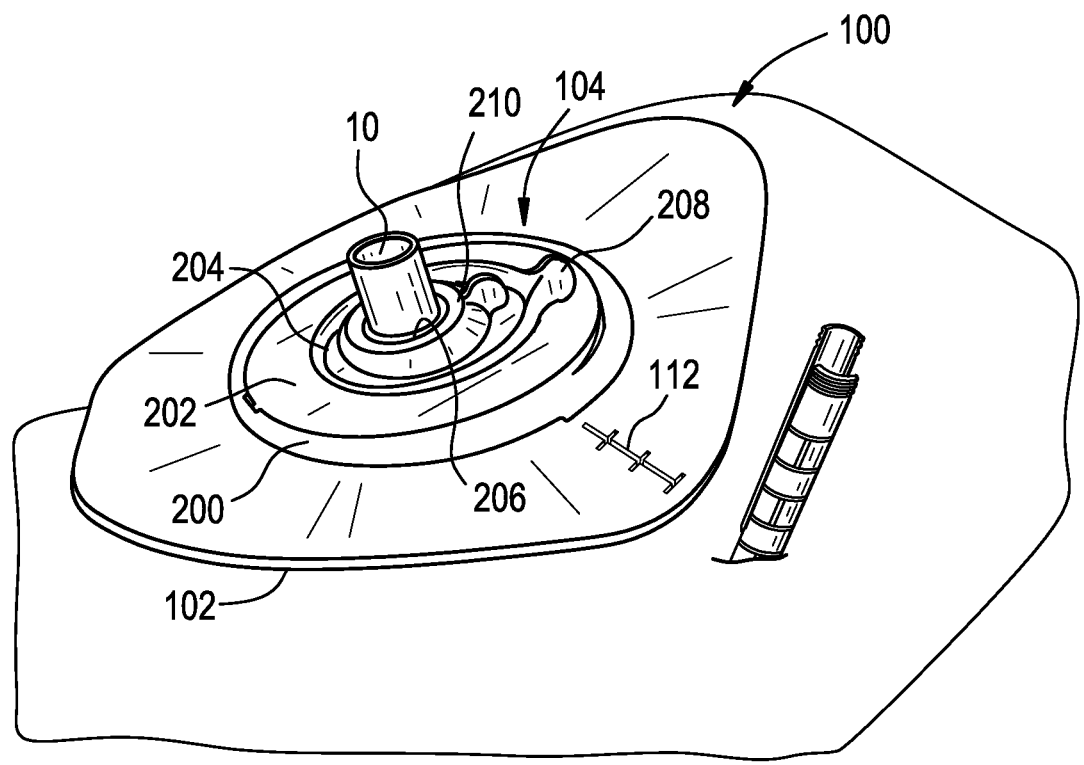
FIG. 26 is a representation of an exemplary surgical application of one embodiment of a surgical access stabilization device.

FIG. 26 shows a first exemplary surgical application of a surgical access stabilization device 100 of the present invention. FIG. 26 shows the surgical stabilization device 100 fully assembled with a port 10, received therein. A distal facing surface of a pad 102 is adhered to the skin of a patient. In this embodiment, the pad 102 is formed as a full patch with a generally oval or egg shape.

Figure 27:
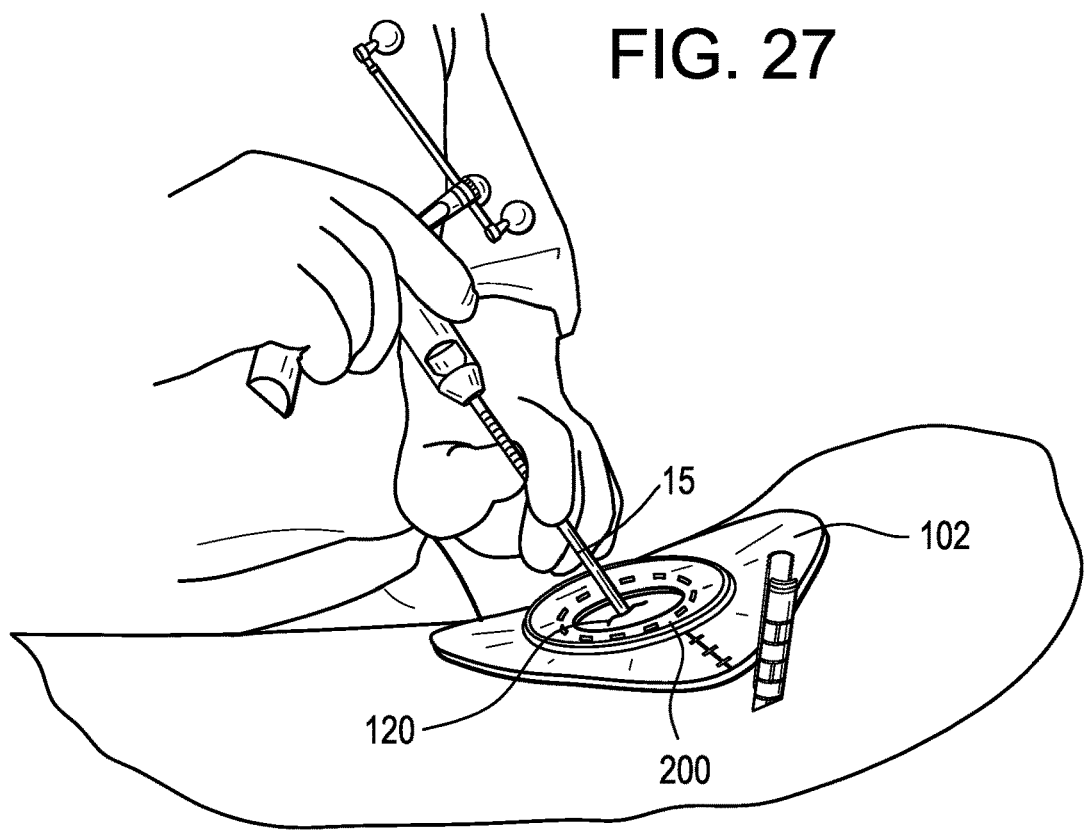
FIG. 27 is a representation of another exemplary surgical application of one embodiment of a surgical access stabilization device.

FIG. 27 shows part of an exemplary method of use of the surgical access stabilization device 100. In FIG. 27, the pad 102 is shown attached to an anchor surface, e.g., the skin of a patient, at a location such that a surgical incision 120 is located within an opening 106 of the pad 102. A base 200 is shown secured to the pad 102. In one embodiment, the pad 102 can be attached to the anchor surface as a stand-alone component. Once attached, the base 200 can then be secured on to a proximal facing surface of the pad 102 by a user. For example, a surgeon can first select, cut, or otherwise manipulate a pad 102 to a desired shape and size for a particular surgical application. Next, an adhesive distal facing side of the pad 102 can be placed at a desired location on the skin of a patient. With the pad securely attached, the base 200 can be moved distally onto pad 102, and can be secured to the pad 102 by engaging complementary engagement features of the base and the pad. For example, slots 209 of the base 200 can be aligned with protrusions 110 of the pad 102. The base can then be secured to the pad 102 with a snap fit.

Alternatively, a base 200 can be secured to a pad 102 prior to adhering the pad 102 to the anchor surface. In one embodiment, a pad and a base can be pre-assembled as a single unitary component for use in a surgical procedure. Alternatively, a pad and a base can be configured as two separate component that are attached prior to a surgical procedure. In this manner, the pad and base can be placed during the surgical procedure as a single assembled unit.

As shown in FIG. 27, a surgeon is manipulating tissue (e.g., navigating to a surgical site, dilating incision 120, etc.) using an instrument 15 inserted through an incision 120 with the pad 102 secured to the engagement surface and the base 200 attached to pad 102. It will be appreciated that the incision 120 can be made either before or after the pad 102 is secured to the anchor surface. Additionally, the incision 120 can be dilated to accommodate a variety of instruments either or before or after the pad 102 has been secured to the engagement surface, and either before or after the base 200 has been attached to the pad 102. Once an incision has been dilated to accommodate a surgical access device, such as a port 10, the port can be inserted through the incision. Again, insertion of the surgical access device can occur either before or after the pad 102 has been secured to the engagement surface, and can occur either before or after the base 200 or any other components of the locking mechanism 104 have been attached.

In one exemplary method, an incision 120 can be made at a desired location on a patient. A pad 102, previously sized and shaped to meet the requirements of a particular surgical procedure or application, can then be secured to the skin of the patient by placing an adhesive distal surface of the pad 102 against a surface of the skin. In other embodiments, a pad of standard size and shape can be intraoperatively cut or otherwise manipulated to meet requirements of a particular surgical procedure or application. The pad 102 can be pre-assembled with the base 200 attached thereto. Alternatively, the base 200 can be attached to the pad 102 once the pad 102 is secured to the skin of the patient. In a preferred embodiment, the pad 102 can be aligned such that incision 120 is centrally located within an opening 106 of the pad 102. With the pad and base surrounding the incision 120, the incision 120 can be prepared to receive a port 10. For example, incision 120 can be dilated using a set of dilating tubes to achieve a desired incision opening. Alternatively, the incision 120 can be prepared for receiving a surgical access device using other methods as is known in the art. Port 10 can then be inserted into the incision 120 using common surgical techniques.

With port 10 inserted, and the base 200 secured on the pad 102, a locking mechanism 104 can be placed in the base 200. The locking mechanism 104 can consist of a retaining ring 202, skirt 204, split ring 206, first locking piece 208 configured to engage with the retaining ring 202, and second locking piece 210 configured to engage with the skirt 204. The port 10 can be positioned at an opening 416 of the split ring 206, and the locking mechanism 104 can be moved distally along the port 10 until a distal facing surface of the locking mechanism 104 contacts a proximal facing surface of the base 200. In one embodiment, a distal facing surface of the skirt 204 can contact a proximal facing surface of the base 200, and the retaining ring 202 can be aligned in an unlocked position with the base 200. To secure the locking mechanism 104, the retaining ring 202 can be rotated from an unlocked position to a locked position. In the unlocked position the radially extending protrusions 502 of the retaining ring can be aligned with the recessed sections 228 of the base, as described above. The retaining ring 202 can then be rotated in a first direction such that the protrusions 502 rotate to engage with transitions 226 of the base extension sections 224. The tab portion 530 of the base 200 can be urged radially outward by a retaining ring protrusion 502 and can remain in an outward position as the protrusion 502 passes fully into the extension section 224. The retaining ring 202 and the base 200 can be configured such that in a locked position, i.e. when a leading edge of the protrusions 502 engage with a transition 226, the protrusion 502 clears the tab portion 230 such that the tab 230 is no longer urged radially outward and can return to its neutral configuration. In this manner, the tab portion 230 can act as a securing mechanism to prevent the retaining ring 202 from being rotated out of the locked position during a surgical application, as the tab 230 and a transition 226 are placed at either end of a protrusion 502 in the locked position. A user can grip features 514 to facilitate smooth and easy rotation of the retaining ring relative to the base. While the above description is provided in connection with assembly of various components, such as the locking mechanism 104, after insertion of the port, it should be appreciated that in some embodiments the port can be inserted through an already-assembled locking mechanism while it is in an unlocked configuration.

With the locking mechanism 104 placed within the base and the port 10 extending therethrough, the port 10 can be adjusted to a desired trajectory, orientation, and location. The port 10 can be adjusted relative to pad 102 in multiple degrees of freedom. For example, port 10 can translate in any radial direction relative to the pad 102. In one embodiment, a surgeon can apply a translation force to a proximal portion of the port 10 by gripping and moving a proximal portion of the port 10 or a handle attached thereto. The skirt 204 can move in accordance with the translational force applied to the port 10. The skirt 204 can translate or slide within the cavity 212 between the base 200 and the retaining ring 202. After achieving a desired positioning of the port 10, the first locking piece 208 can be rotated in a first direction to clamp the skirt 204 at the desired position within the cavity 212, thereby restricting in a radial direction further translational movement of the skirt, and thus the attached port 10. Rotating first locking piece 208 in the second direction can move the first locking piece proximally from the base and thus release the clamped skirt 204, permitting translational movement of the skirt, and thus the attached port 10.

Port 10 can also be angulated, rotated, or longitudinally translated relative to pad 102. For example, port 10 can be rotated 360 degrees by gripping a proximal portion of port 10 and rotating the port. Split ring 206, with rounded outer edge 402, can rotate 360 degrees within the tapered inner surface 324 of opening 316 of skirt 204. Furthermore, port 10 can be angled to a variety of desired orientations by gripping a proximal portion of port 10 and angling the port with respect to pad 102. Again, the rounded outer edge 402 of split ring 206 can be angled with respect to tapered inner surface 324 of opening 316 of skirt 204.

A port 10 can also be translated in a longitudinal direction relative to a pad 102 by applying a force in a proximal or distal direction to the proximal end of the port 10 such that the port 10 translates in a proximal or distal direction relative to the pad 102. Once a desired orientation and positioning of the port 10 is achieved relative to the pad 102, a second locking piece can be rotated in a first direction to restrict further rotational, angular, or translational movement. In one embodiment, as the second locking piece is rotated in the first direction, the second locking piece moves distally and applies an inward compressive force to the skirt extension 320. As the skirt extension 320 is compressed radially inward, the skirt extension is compressed onto the split ring 206 with port 10 placed therein. After rotating the second locking piece a first amount, the compressive force applied by the second locking piece restricts translational movement of the port in the longitudinal direction. After rotating the second locking piece further to a second amount, the compressive force applied by the second locking piece can restrict rotational movement of the port with respect to the pad by restricting the ability of inner ring 206 to rotate relative to the inner extension of 320 of skirt 204. Upon rotating the second locking piece further to a third amount, the compressive force applied by the second locking piece can restrict angular movement of the port relative to the pad, by restricting the ability of split ring 206 to be angled relative to the extension 320 of skirt 204. Rotating the second locking piece in a second direction moves the second locking mechanism proximally relative to inner extension 320 of the skirt 304 and reduces the inward compressive force on the skirt 204 and thus on the split ring 206 and port 10, received therein. As the second locking piece is rotated in the second direction, port 10 can move relative to pad 102. In this manner, the second locking piece can be used to selectively restrict translational, rotational, and angular movement of the port relative to the pad. The locking mechanism 104 can be unlocked during a surgical procedure to permit for adjustment of port 10, and re-locked to secure the port in a different location or trajectory if desired.

Figure 28:
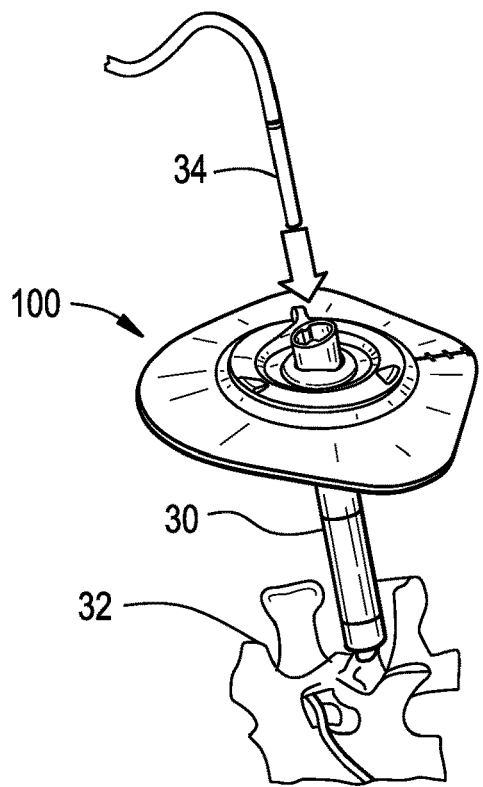
FIG. 28 is a graphical representation of a surgical access stabilization device of the present invention in use in a spinal procedure with a rigid port tube disposed therein.

With port 10 established and stabilized at a desired location and trajectory, various instruments, implants and the like can be passed percutaneously though port 10 to a surgical site. For example, as shown in FIG. 28, surgical access device can be a port tube 30 used to access a surgical site located at a spinal region 32. An instrument 34 can be inserted through port tube 30. The instrument 34 can be any variety of instruments, such as a camera or an implant. In one embodiment port tube 30 can be a 15 mm rigid port, sized to accommodate any variety of objects including, for example, larger implants. An inner lumen of port tube 30 can be sized to facilitate insertion of a variety of instruments, implants and the like having various shapes. As such, a non-circular inner lumen geometry can be preferred.

Figure 29:
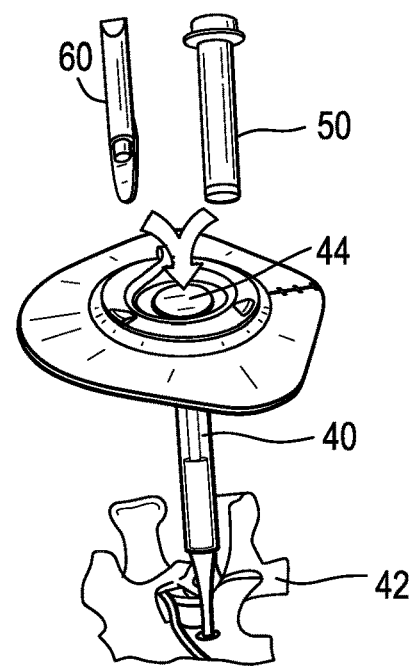
FIG. 29 is a graphical representation of a surgical access stabilization device of the present invention in use in a spinal procedure with a flexible barrier port disposed therein.

FIG. 29 shows an exemplary application of surgical access stabilization device 100 configured to receive a soft mesh port 40. In the embodiment of FIG. 29, locking mechanism 104 can be adapted to receive a flex port or other surgical access device by including a cap member 44 to secure and selectively close an opening to the surgical access device. Cap member 44 can be removed from a proximal end of the surgical access device such that instruments, implants, and the like may percutaneously pass to a surgical site 42. In some procedures it can be desirable to use a flex port to minimize trauma to surrounding tissue. In one embodiment flex port can be a 5 mm flex port, sized and configured to receive, among other things, visualization instruments, optical trocars, and medium sized implants. In another embodiment, flex port can be a 4 mm flex port, sized and configured to receive, among other things, small expanding implants, optical trocars, and visualization instruments.

Variations can be made to the above described methods and devices and are considered within the scope of the present invention. For example, locking mechanism 104 can be placed in base 200 and secured therein before port 10 is inserted into an incision 120. In such an embodiment, port 10 can be inserted into the incision 120 by moving the port distally through central opening 101 of the surgical access device. By way of further example, first and second locking pieces can take forms other than locking rings, and selectively locking a port relative to a pad can be achieved through means of operating first and second locking mechanism, other than rotation. By way of non-limiting example, a locking mechanism of the present invention can include any number of removable adhesive adjustment sites, threaded locking knobs, or lever action tightening wheels. Furthermore, as referenced above, locking mechanism 104 need not have a separate first and second locking piece. In one embodiment a single locking piece can be used to selectively restrict movement of port 10 relative to pad 102. Regardless of the configuration used, locking mechanism 104 is configured to couple and selectively lock a surgical access device with respect to a pad.

Figure 30:
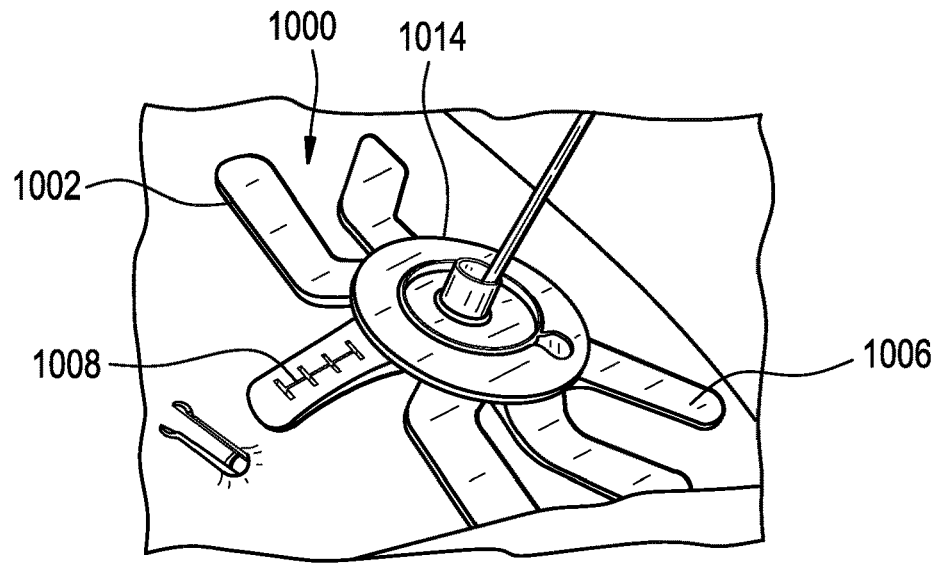
FIG. 30 is a representation of an exemplary surgical application of another embodiment of a surgical access stabilization device.

In a surgical access stabilization device of the present invention, a foundation pad can have a variety of shapes and sizes according to the geometry of the application area or needs of a user. In a surgical application, the particular shape and size of the pad can depend on a variety of factors including size of the patient, location of a surgical site, size of an incision, size of an area to be treated, range of motion required by a surgeon to complete the procedure, etc. FIG. 30 shows one embodiment of a surgical access stabilization device 1000 including a pad 1002 and a locking mechanism 1014 placed on a central portion, not shown, of pad 1002. Pad 1002 can have at least one radial finger 1004 extending from the central portion. Navigational markings 1008 can be included on one of the at least one radial fingers 1004. In the embodiment shown, pad 1002 has 8 radial fingers 1004. Each radial finger 1004 can be sized and shaped as desired or as required by a particular application.

Figure 31:
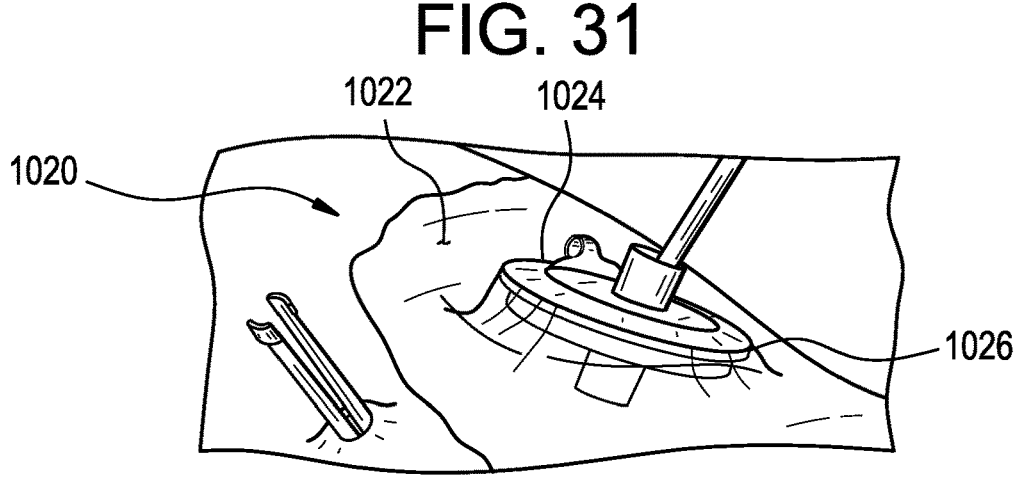
FIG. 31 is a representation of an exemplary surgical application of another embodiment of a surgical access stabilization device.

In another exemplary embodiment, shown in FIG. 31, a surgical access device 1020 can include a pad 1022 formed from a thin polymer with an adhesive distal facing surface. In one embodiment, the thin polymer pad can be a rubber, neoprene, PTFE, etc. The pad 1022 can have a thickness between about 1 mm and about 5 mm, and, in some embodiments, a thickness of between about 1.5 mm and about 3.5 mm. In the embodiment shown in FIG. 31, at least a portion of a locking mechanism 1024 can be placed between an anchor surface, i.e., the skin of a patient, and the adhesive distal facing surface of pad 1022. For example, base 1026 of locking mechanism 1024 can be placed such that a distal surface of base 1026 is in contact with the anchor surface. The pad 1022 can then be placed over the anchor surface and the base 1026 such that base 1026 is held secure to the anchor surface by pad 1022. The locking mechanism 1024 can be attached to base 1026 in a manner as described above.

Figure 32:
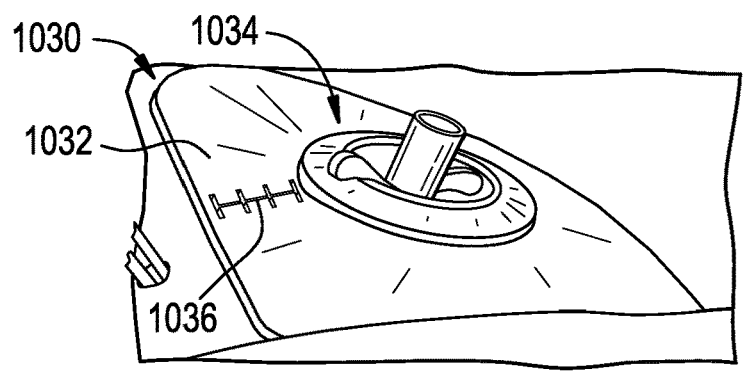
FIG. 32 is a representation of an exemplary surgical application of another embodiment of a surgical access stabilization device.

FIG. 32 shows yet another exemplary embodiment of a surgical stabilization device 1030 of the present invention. Surgical access stabilization device 1030 includes a pad 1032 configured as a full patch having a generally rectangular shape. A locking mechanism 1034 is shown at a central location of pad 1032. Alternatively, locking mechanism 1034 can be received at any location on pad 1032. Pad 1032 can include navigational markings such as markings 1036 to aid in alignment and placing of pad 1032 relative to surgical or anatomical structures.

Figure 33:
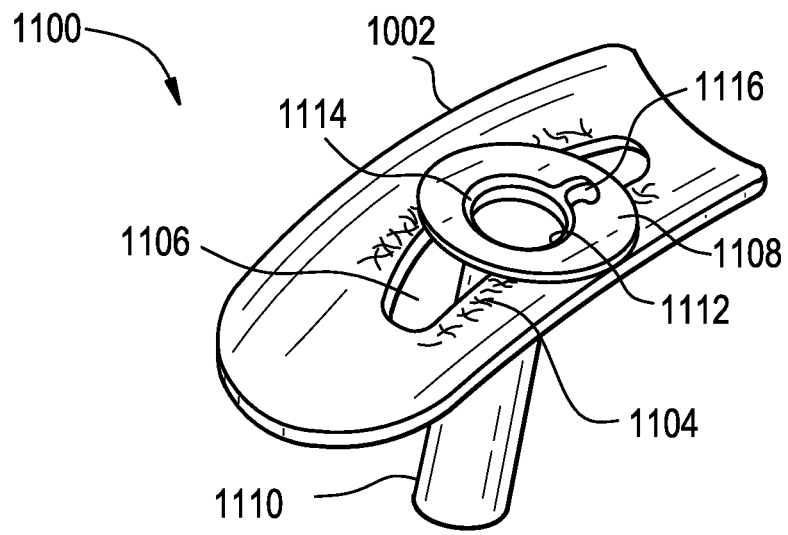
FIG. 33 is a perspective view of another embodiment of a surgical access stabilization device having a surgical access device disposed therein.
Figure 34:
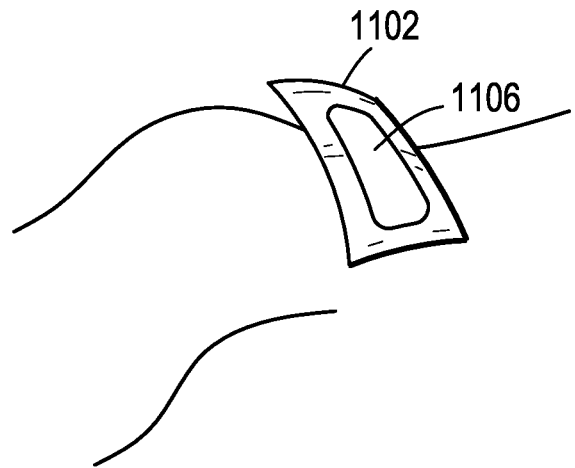
FIG. 34 is a representation of an exemplary foundation pad of the surgical access stabilization device of FIG. 33.

FIGS. 33 and 34 illustrate a second exemplary embodiment of a surgical access stabilization device of the present invention. As shown in FIG. 33, a surgical access stabilization device 1100 can comprise a pad 1102 configured to receive a surgical access device, e.g., a port 1110. A locking mechanism can couple port 1110 to pad 1102 and selectively lock movement therebetween. Pad 1102 can have an adhesive distal facing surface configured to contact an anchor surface. In a preferred embodiment, the adhesive distal facing surface of pad 1102 can comprise a medical grade adhesive contacting layer to contact skin of a patient.

Pad 1102 can have an opening 1106 configured to receive a surgical access device. In a preferred embodiment, opening 1106 can be an elongate slot extending along pad 1102. For example, with reference to FIG. 34, pad 1102 can have an opening 1106 extending along a longitudinal axis of the pad. In one embodiment, pad 1102 can be generally rectangular in shape. As shown in FIG. 34, opening 1106 can have a similar or complementary shape to that of pad 1102. Alternatively, opening 1106 can have a different shape than that of pad 1102. One having ordinary skill in the art will appreciate that the pad 1102 and opening 1106 can have any of a variety of shapes.

An elongate slot opening 1106 can beneficially favor adjustment of a surgical access device in a transverse plane during a surgical procedure. Such adjustment permits gross changes to angulation of a surgical access device. For example, in a spinal surgery application, it can be desirable to move a surgical access device in a transverse direction. As such, pad 1102 can be placed such that elongate opening 1106 extends in a transverse plane (e.g., extending medially and laterally). In this manner, a port can be adjusted to allow for gross changes in angulation. For example, the port can be placed for a 25 degree TLIF access or a 45 degree Kambin's access to a spinal surgical site.

A base 1108 can be configured to receive port 1110 through a central opening of the base. Alternatively, base 1108 can be integrally formed with port 1110 in the form of a flange extending from a proximal end of the port 1110. Further, base 1108 can be a single component, for example as shown in FIG. 33, or base 1108 can be multiple components. For example, base 1108 can be configured similar to a skirt 104, described above, with a split ring similar to inner split ring 106, described above, to receive port 1110.

A locking mechanism can be configured to selectively restrict movement of port 1110 with respect to pad 1102. In one embodiment, locking mechanism 1104 can be a removable adhesive. By way of non-limiting example, the locking mechanism can be a hook and eye closure. For example, one side of the hook and eye closure can be placed on a proximal facing surface of the pad 1102 near at least a portion of the opening 1106. A corresponding side of the hook and eye closure can be placed on a distal facing surface of base 1108. In this manner, base 1108 can be removably secured to pad 1102 by engaging the two corresponding portions of the hook and eye closure. Base 1108, with inserted port 1110, can be repeatably placed and removed at a number of locations along opening 1106 as desired. It will be appreciated that any other form of removable adhesive can be used in a similar manner.

In some embodiments, at least one addition locking piece 1112 can be used to further selectively restrict motion of the port 1110 with respect to pad 1102. In one embodiment, locking piece 1112 can be a locking ring with external threads 1114 configured to engage with corresponding threads on an inner surface of base 1108. Grip 1116 can extend proximally from locking piece 1112 to aid a user in rotating the locking piece to selectively restrict rotational, angular, and longitudinal translation movement of the port relative to pad 1102. It will be appreciated that locking piece 1112 can be configured similar to one of the first and second locking pieces as described previously herein.

FIG. 34 illustrates an exemplary positioning of a surgical access stabilization device of the second embodiment. Pad 1102 can be placed such that pad 1102 extends laterally along a transverse axis of a patient. In one application involving a spinal surgical site, the pad 1102 can be placed laterally in a lumbar region of a patient. Opening 1106 can extend laterally along pad 1102 such that a base 1108 with a port received therein can be selectively moved and adjusted along the transverse plane. In this manner a surgeon can achieve gross changes to angulation of the port during a surgical procedure without having to remove a stabilization device or create a further incision.

Figure 35:
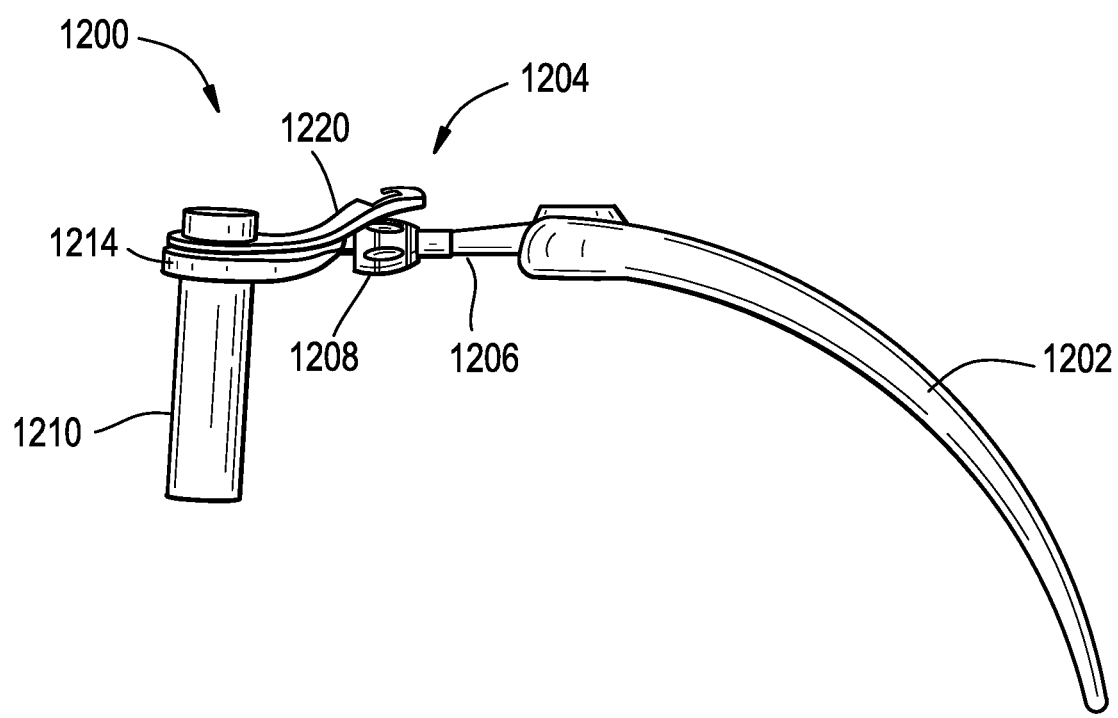
FIG. 35 is a representation of another embodiment of a surgical access stabilization device having a surgical access device disposed therein.
Figure 36:
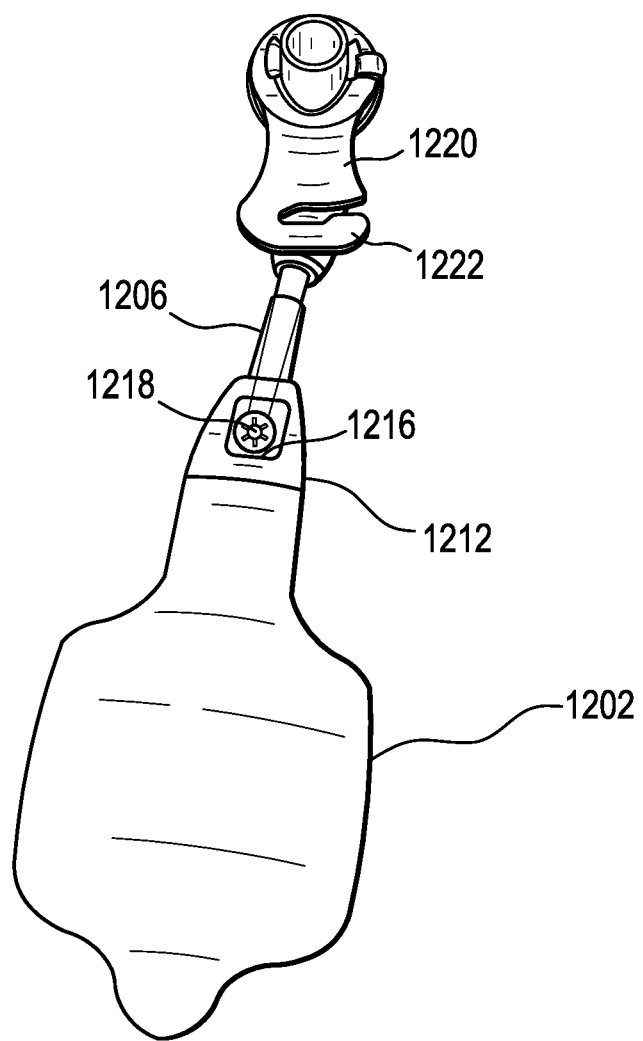
FIG. 36 is another view of the surgical access stabilization device of FIG. 35.

Another exemplary embodiment of a surgical access stabilization device according to the present invention is shown in FIGS. 35 and 36. In some applications it may be undesirable to place an adhesive pad near a surgical site or incision used to access same. For such a situation, a surgical access stabilization device of the present invention can be used to couple a surgical access device to a remotely located foundation pad to place the surgical access device at a location a distance away from the pad.

A surgical access stabilization device 1200 can have a connecting mechanism 1204 configured to connect a surgical access device, e.g., port 1210, to a pad 1202. In one embodiment connecting mechanism 1204 can include an arm 1206 with a connector 1208 and an attachment component 1214. Attachment component 1214 can have a central opening to receive a surgical access device 1210. Connector 1208 can be located at a first end of arm 1206, and can be configured to engage a portion of attachment component 1214. A second end of arm 1206 can be attached to pad 1202 such that arm 1206 couples the surgical access device to the pad.

As shown in FIG. 36, pad 1202 can be similar to the pads described above. In one embodiment, pad 1202 can be an expansive flexible pad having an adhesive distal facing surface. Pad 1202 can have an attachment portion 1212 configured to couple with a portion of connecting mechanism 1204, as will be described below. Pad 1202 and arm 1206 can be formed integrally as one component or can be configured to be connected via one or more connection features. In one embodiment, an opening 1216 can be formed in the attachment portion 1212 and can be configured to receive a fastener 1218 of arm 1206. It will be appreciated that pad 1202, and opening 1216, can take on any variety of shapes and sizes as required by a particular application. Pad 1202 can be coupled to arm 1206 in any number of known coupling methods. In one embodiment, as shown in FIG. 36, fastener 1218 can be a threaded screw fastener. Fastener 1218 can be placed within opening 1216 and engaged therein using a screw feature of the fastener 1218. Non-limiting examples of alternative fasteners include a snap mechanism, complementary male and female component interference fit, screws, threaded fasteners, etc.

Arm 1206 can be made of a malleable material such that the arm can be bent to adjust positioning of the first end relative to the second end. In this manner, a surgical access device connected to the first end of the arm can be placed in a desired position relative to a pad coupled to the second end of the arm by bending the arm to a desired configuration. In one embodiment, connector 1208 can be located on the first end of arm 1206 to engage with an attachment piece 1214 to couple the port 1210 to the first end of the arm. Connector 1208 can engage attachment piece 1214 by any means of connecting as is known in the art. For example, in one embodiment, connector 1208 can be a ball joint connector and can receive an extension of attachment piece 1214 within a recess of the ball joint connector to secure attachment piece 1214 to arm 1206.

A handle 1220 can be associated with port 1210 and aid in movement, for example rotational movement, of the port. In one embodiment, port 1210 can be inserted through an opening in the handle 1220. The handle can have a grip portion 1222 extending radially outward from the opening. Grip 1222 can include features to facilitate rotational movement of the port 1210. For example, the grip can have a slot for an instrument or a tab for a user to grasp. Rotational motion of the grip can translate into accompanying rotational motion of the inserted port.

Figure 37:
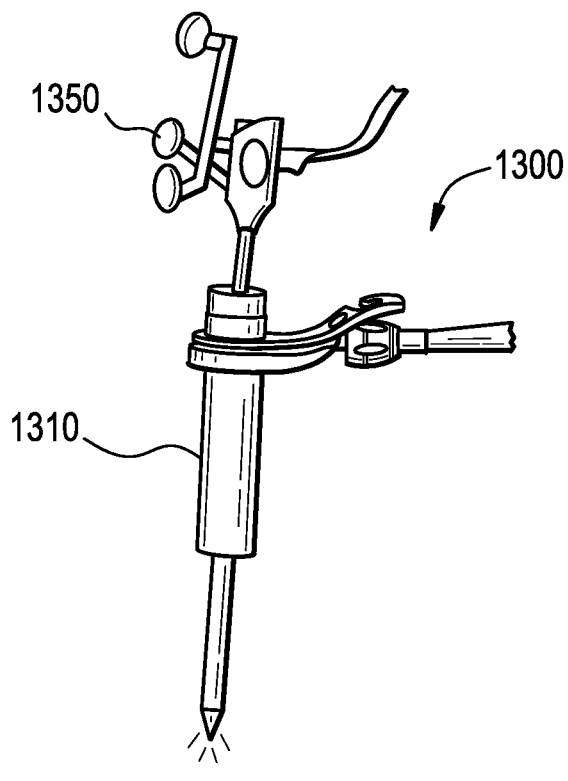
FIG. 37 is a representation of another exemplary surgical application of the surgical access stabilization device of FIG. 35.
Figure 38:
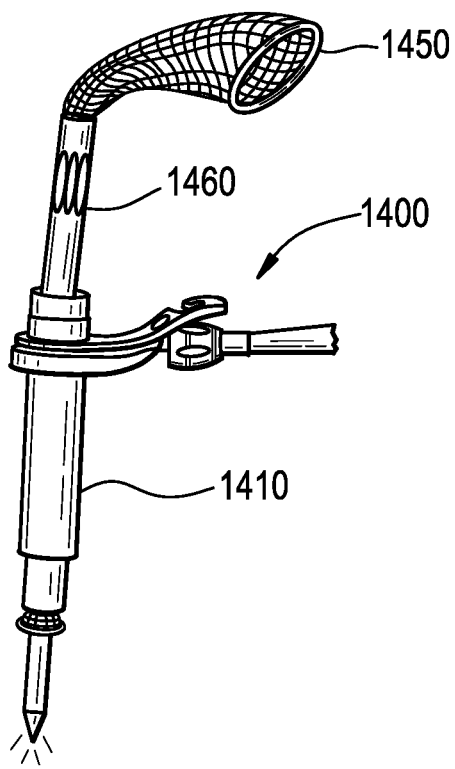
FIG. 38 is a representation of another exemplary surgical application of the surgical access stabilization device shown in FIG. 35.

FIGS. 37 and 38 show an exemplary use of a port once placed in a stabilized position using a surgical access stabilization device of the present invention. While FIGS. 37 and 38 depict a surgical access stabilization device of an embodiment having a bendable arm connected to the port, it will be understood that any of the embodiments described herein can be used to stabilize a port. FIGS. 37 and 38 illustrate that the port can be used to pass any of a variety of instruments, implants, or objects percutaneously through a stabilized port to a target surgical site. For example, as shown in FIG. 37 port 1310 can be secured by a surgical access stabilization device 1300. With port 1310 stabilized, an elongate tool or other instrument with a navigational array 1350 can be inserted percutaneously through port 1310 to a target site. By way of further non-limiting example, FIG. 38 illustrates a port 1410 secured by a surgical access stabilization device 1400. With port 1410 secured, a protective mesh 1450 can be inserted through the port to a target site to reduce trauma to surrounding tissue. Further instrumentation, such as needle 1460, or other objects can then be passed percutaneously through port 1410 and mesh 1450.

Figure 39:
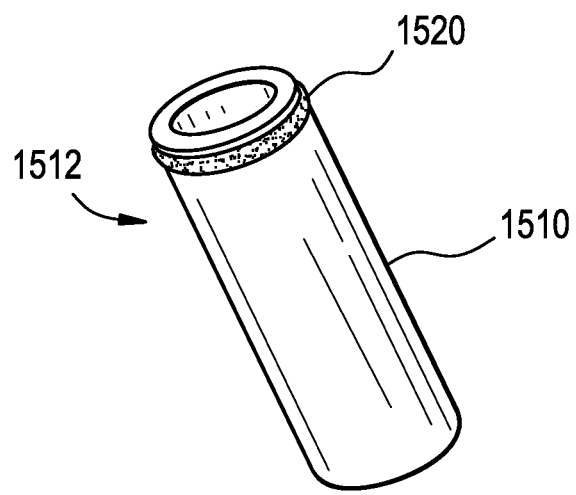
FIG. 39 is an illustration of another embodiment of a surgical access device of a surgical access stabilization device of the present invention.

In another possible variation of the above described methods and devices, a surgical access device can have a pad attached to a proximal portion of the surgical access device, such that the pad can be deployed to adhere to an anchor surface. In one embodiment, as shown in FIG. 39, a surgical access device port 1510 can have an adhesive pad 1520 attached at a proximal end 1512 of the port. The adhesive pad 1520 can be attached to the proximal portion 1512 of the port, such that the pad can be deployed from the proximal portion of the port to adhere to an anchor surface, e.g., a patient's skin, after the port is inserted within an incision in the patient. The adhesive pad 1520 can be any of the pads described above. For example, in one embodiment, the pad 1520 can be a continuous pad which, in the pad's deployed state, can cover an entire sterile drape opening. In other embodiments, an adhesive pad can include one or more extensions, fingers, or tethers which can be arranged in a deployed or non-deployed state.

In a non-deployed state, or an insertion state, the adhesive pad can be arranged in a compact manner and can be attached or secured to a proximal portion of a port while the port is inserted through an incision. Alternatively, the pad can be attached or secured in the non-deployed state to the proximal portion of the port after the port has been inserted within the incision. For example, the pad can be snapped on to a proximal portion of the port in the non-deployed state, before or after the port is inserted within an incision. The pad can then be deployed such that a distal facing adhesive surface of the pad can adhere to the anchor surface. In one embodiment, the pad can be deployed by rolling or moving the pad, or a portion of the pad, distally towards the anchor surface. Alternatively, an engagement mechanism between the pad and the port can be released such that the pad, or a portion of the pad, is no longer secured to the port and can be manipulated by a surgeon to secure the distal facing adhesive side of the pad to the anchor surface. By way of non-limiting example, the engagement mechanism can be a snap, screw, lever, tension member, or other engagement mechanism as is known in the art.

Figure 40:
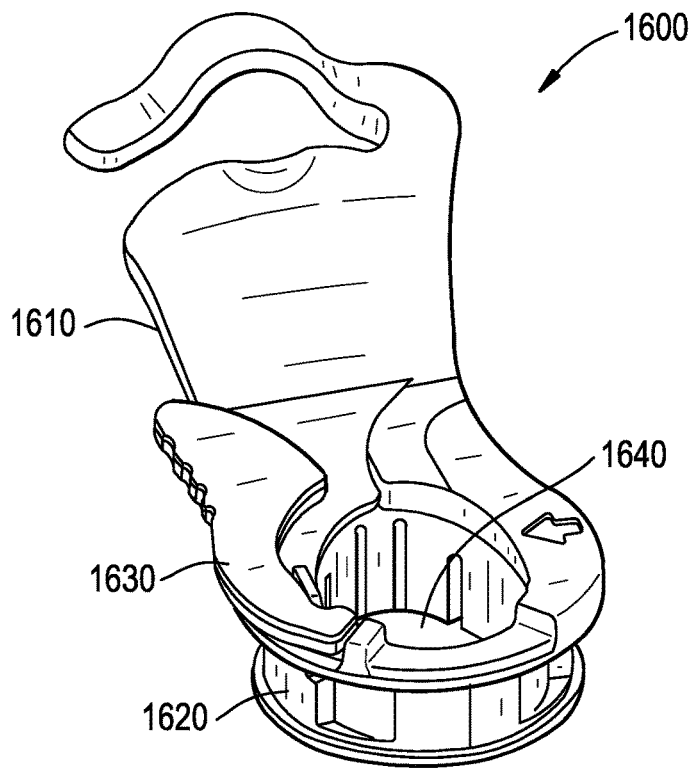
FIG. 40 is a perspective view of another embodiment of a handle of a surgical access stabilization device of the present invention.
Figure 41:
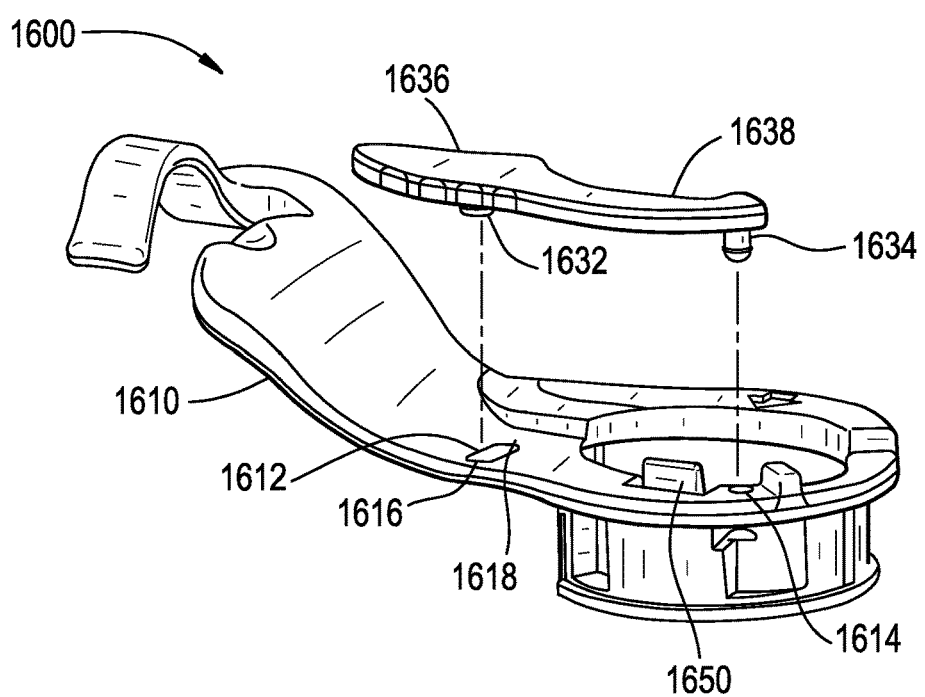
FIG. 41 is an exploded view of the handle of FIG. 40.
Figure 42:
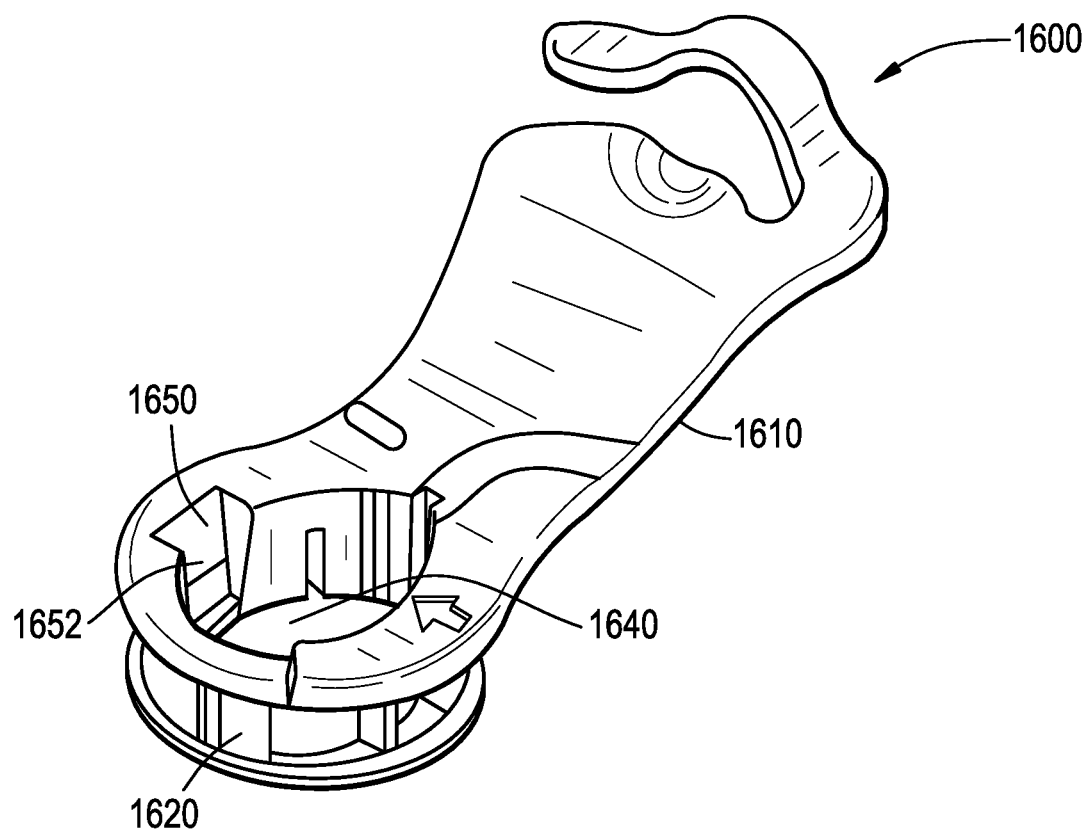
FIG. 42 is a perspective view of a body of the handle of FIG. 40.

FIGS. 40-42 show another embodiment of a handle 1600 of a surgical access stabilization device of the present invention. For example, the handle of FIGS. 40-42 can be associated with a surgical access device, similar to how the handle 1220 is shown and described in association with the port 1210 in FIGS. 35-36. The handle 1600 can include a main body portion 1610 having an extension 1620 and a lever 1630. In one embodiment, the extension 1620 can be generally cylindrical and extend distally from a main body 1610 of the handle. The extension 1620 can define a through hole 1640 through which a surgical access device, such as, for example, a port, can be inserted. It will be appreciated that the through hole 1640 can have any of a variety of geometries such that a desired surgical access device can pass therethrough. As can best be seen in FIG. 42, the handle 1600 can include a locking portion 1650 that can engage with features of a surgical access device to selectively maintain relative positioning between the surgical access device and the handle 1600. In one embodiment, the locking portion 1650 can be a zip-tie or ratchet/pawl style snapping lever having one or more teeth 1652 that can engage with features on an outer surface of a surgical access device. For example, in one embodiment, the one or more teeth 1652 of the locking portion 1650 can selectively engage with one or more grooves formed on an outer surface of a surgical access device when the surgical access device is disposed within a through hole 1640. In some embodiments, the locking portion 1650 can include a tab or lever biased to engage with a surgical access device without user interaction. And, in some embodiments, the one or more teeth 1652 can be configured to allow movement in a first direction while preventing movement in a second direction (e.g., permitting distal advancement of a surgical access device through the through hole 1640 while preventing proximal retraction).

FIG. 41 shows the lever 1630 of FIG. 40 separated from the main body 1610. The lever 1630 can selectively engage the locking portion 1650 to move the locking portion out of engagement with a surgical access device within the through hole 1640 of the handle 1600, thereby acting as a release to allow adjustment of a surgical access device relative to the handle.

In one embodiment, the lever 1630 can be a generally planar element with at least one engagement feature extending from a distal facing surface thereof. In the embodiment shown in FIG. 41, a first post 1632 can extend from a distal facing surface of a first planar portion 1636 and can be received within a slot 1612 in the main body 1610. A second post 1634 can extend from a distal facing surface of second planar portion 1638 and can be received within a hole 1614 in the main body. To insert the lever 1630 into the main body 1610, lever engagement features, such as the posts 1632, 1634, can be moved into main body receiving features, such as the slot 1612 and the hole 1614. In one embodiment, the engagement features of the lever can snap into the receiving features of the main body. A slot 1612 of the main body can have a first end 1616 and a second end 1618. The first end 1616 of the slot 1612 can be located closer to an edge of the main body 1610 than the second end 1618 of the slot. In other words, the slot 1612 can extend from a position close to an edge of the main body 1610 laterally inwards towards a center of the main body. It will be appreciated that, while an embodiment of the handle 1600 shown in FIG. 41 has two engagement features and corresponding receiving features, a lever and a main body of the handle can have any number of engagement features and receiving features.

With the lever 1630 inserted in the main body 1610, as shown, for example, in FIG. 40, a user can engage the lever such that the lever moves the locking portion 1650 to selectively engage a surgical access device disposed in the through hole 1640. For example, a force can be applied to the lever 1630 such that the first post 1632 translates within the slot 1612. The second post 1634 of the lever can remain fixed within the hole 1614 of the main body, such that the lever can pivot about the second post as the first post 1632 translates within the slot 1612 in the main body 1610. In one embodiment, a user can depress the lever by applying a force to the first planar portion 1636 of the lever in an inward direction, i.e., towards a center line of a main body 1610, causing the first post 1632 to translate within the slot 1612 and pivoting the lever about the second post 1634. With the lever depressed, the second planar portion 1638 of the lever can engage the locking portion 1650 of the main body 1610 to deflect the locking portion to a position where the one or more teeth 1652 disengage from the one or more grooves formed on a surgical access device disposed in the through hole 1640. In one embodiment, the lever 1630 can return to the position illustrated in FIG. 40 when a user releases the above-described force. That is, the lever 1630 can pivot about the post 1634 such that the first planar portion 1636 moves radially outward. Such a movement allow the locking portion 1650 to move back to a position (e.g., via a biasing force, etc.) where the one or more teeth 1652 engage with the one or more grooves or other features formed on a surgical access device disposed in the through hole 1640.

It will be appreciated that the handle 1600 of FIGS. 40-42, and various components thereof, can be associated with a port in a number of different ways within the scope of the present invention. For example, a zip-tie or ratchet/pawl style snapping lever can be used as a component of a locking mechanism of the present invention in place of a split ring to selectively restrict axial motion of a surgical access device. By way of further example, the handle 1600 can be used in any of the various embodiments described herein. Furthermore, engagement features of a lever and receiving features of a main body can be formed as any complementary features such that a lever can be coupled to a main body of a handle and movable between an open position, in which a locking portion of the handle is not engaged, and a closed position, in which the locking portion of the handle is engaged.

The above exemplary embodiments describe a spinal surgical application. While this is one contemplated use, the methods and devices of the present invention can be equally adapted for use in other areas of a patient's body. As such, the devices described herein can be formed in a variety of sizes and materials appropriate for use in various areas of a patient's body.

One skilled in the art will appreciate further features and advantages based on the above-described embodiments. Accordingly, the disclosure is not to be limited by what has been particularly shown and described. All publications and references cited herein are expressly incorporated herein by reference in their entirety.

The invention claimed is:

1. A surgical access stabilization system, comprising:
a surgical access device configured to be received in a body of a patient, the surgical access device having a lumen formed therein configured to receive one or more instruments therethrough;
a pad having a proximal surface and a distal surface; and
an arm coupled directly to the pad, the arm having a connector and an attachment component, the attachment component having an opening formed therein for receiving the surgical access device therethrough and the connector being disposed between a first end of the arm and the attachment component,
wherein the connector is a ball joint connector that is configured to receive an extension of the attachment component within a recess of the ball joint connector to secure the attachment component to the arm.

2. The system of claim 1, wherein the pad is remotely located from the surgical access device such that the surgical access device is positioned at a location a distance away from the pad.

3. The system of claim 1, wherein the pad further comprises an attachment portion having an opening formed therein, the opening being configured to receive a fastener of the arm to couple the pad to the arm.

4. The system of claim 1, wherein the surgical access device is configured to translate relative to the attachment component when disposed therein.

5. The system of claim 1, further comprising a handle associated with the surgical access device, the handle having an opening configured to receive a portion of the surgical access device therethrough.

6. The system of claim 5, wherein the handle further comprises a grip portion extending radially outward from the opening, the grip portion having one or more surface features configured to facilitate rotational movement of the surgical access device.

7. The system of claim 6, wherein the one or more surface features include one or more of a slot for an instrument or a tab configured to be grasped by a user.

8. The system of claim 6, wherein rotational motion of the grip portion translates into accompanying rotational motion of the inserted surgical access device.

9. The system of claim 1, wherein the distal surface of the pad further comprises an adhesive.

10. The device of claim 1, wherein a locking mechanism can selectively lock any of rotational movement of the surgical access device and angular movement of the surgical access device.

11. The system of claim 1, wherein the connector separates the first end of the arm from the attachment component and is configured to engage an outer surface of the arm.

12. A surgical access stabilization system, comprising:
a surgical access device configured to be received in a body of a patient, the surgical access device having a lumen formed therein configured to receive one or more instruments therethrough;
a pad having a proximal surface and a distal surface; and
an arm coupled to the pad, the arm having a connector and an attachment component, the attachment component having an opening formed therein for receiving the surgical access device therethrough and the connector being disposed between a first end of the arm and the attachment component;
wherein the connector is capable of angulating with respect to a central longitudinal axis of the surgical access device.

13. The system of claim 12, wherein the connector is a ball joint connector that is configured to receive an extension of the attachment component within a recess of the ball joint connector to secure the attachment component to the arm.

14. A surgical access stabilization system, comprising:
a surgical access device configured to be received in a body of a patient, the surgical access device having a lumen formed therein configured to receive one or more instruments therethrough;
a pad having a proximal surface and a distal surface, the pad including an attachment portion having an opening formed therein, the opening being configured to receive a fastener of the arm to couple the pad to the arm; and
an arm coupled to the pad, the arm having a connector and an attachment component, the attachment component having an opening formed therein for receiving the surgical access device therethrough and the connector being disposed between a first end of the arm and the attachment component.

15. A surgical access stabilization system, comprising:
a surgical access device configured to be received in a body of a patient, the surgical access device having a lumen formed therein configured to receive one or more instruments therethrough;
a pad having a proximal surface and a distal surface; and
an arm coupled directly to the pad, the arm having a connector and an attachment component, the attachment component having an opening formed therein for receiving the surgical access device therethrough and the connector being disposed between a first end of the arm and the attachment component,
wherein the pad further comprises an attachment portion having an opening formed therein, the opening being configured to receive a fastener of the arm to couple the pad to the arm.

16. A surgical access stabilization system, comprising:
a surgical access device configured to be received in a body of a patient, the surgical access device having a lumen formed therein configured to receive one or more instruments therethrough;
a pad having a proximal surface and a distal surface;
an arm coupled directly to the pad, the arm having a connector and an attachment component, the attachment component having an opening formed therein for receiving the surgical access device therethrough and the connector being disposed between a first end of the arm and the attachment component; and
a handle associated with the surgical access device, the handle having an opening configured to receive a portion of the surgical access device therethrough.

* * * * *